US012060596B2

(12) United States Patent
Foster et al.

(10) Patent No.: US 12,060,596 B2
(45) Date of Patent: Aug. 13, 2024

(54) **MATERIALS AND METHODS FOR CONTROLLING LIMITATION CONDITIONS IN PRODUCT BIOSYNTHESIS FOR NON-PHB GENERATING SPECIES OF THE GENERA *RALSTONIA* OR *CUPRIAVIDUS* AND ORGANISMS RELATED THERETO**

(71) Applicant: INV NYLON CHEMICALS AMERICAS, LLC, Wilmington, DE (US)

(72) Inventors: Alexander Brett Foster, Redcar (GB); Cristina Serrano Amatriain, Redcar (GB); Gary J. Smith, Redcar (GB); Paul Sheldon Pearlman, Thornton, PA (US); Mark Paul Taylor, Redcar (GB); Jonathan Combe, Redcar (GB); Daniel Bawdon, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

(21) Appl. No.: 16/399,145

(22) Filed: Apr. 30, 2019

(65) Prior Publication Data
US 2019/0352674 A1 Nov. 21, 2019

Related U.S. Application Data

(60) Provisional application No. 62/665,751, filed on May 2, 2018.

(51) Int. Cl.
| | |
|---|---|
| *C12P 7/625* | (2022.01) |
| *C12N 1/20* | (2006.01) |
| *C12N 9/04* | (2006.01) |
| *C12N 9/10* | (2006.01) |
| *C12N 9/88* | (2006.01) |
| *C12P 7/04* | (2006.01) |
| *C12P 7/06* | (2006.01) |
| *C12P 7/42* | (2006.01) |

(52) U.S. Cl.
CPC ............ *C12P 7/625* (2013.01); *C12N 1/20* (2013.01); *C12N 9/0006* (2013.01); *C12N 9/1029* (2013.01); *C12N 9/13* (2013.01); *C12N 9/88* (2013.01); *C12P 7/04* (2013.01); *C12P 7/065* (2013.01); *C12P 7/42* (2013.01); *C12Y 101/01001* (2013.01); *C12Y 203/01016* (2013.01); *C12Y 208/03015* (2013.01); *C12Y 401/01004* (2013.01); *C12N 2500/02* (2013.01); *C12N 2500/05* (2013.01); *C12N 2500/12* (2013.01); *C12N 2500/24* (2013.01)

(58) Field of Classification Search
None
See application file for complete search history.

(56) References Cited

U.S. PATENT DOCUMENTS

| | | |
|---|---|---|
| 3,957,876 A | 5/1976 | Rapoport et al. |
| 4,554,101 A | 11/1985 | Hopp |
| 6,207,217 B1 | 3/2001 | Peoples et al. |
| 6,888,034 B1 | 5/2005 | Landray et al. |
| 7,384,783 B2 | 6/2008 | Kunas et al. |
| 8,603,518 B2 | 12/2013 | Boon et al. |
| 8,809,027 B1 | 8/2014 | Lynch et al. |
| 8,986,960 B2 | 3/2015 | Sichwart |
| 9,221,737 B2 | 12/2015 | Valdez |
| 9,580,733 B2 | 2/2017 | Botes et al. |
| 9,637,764 B2 | 5/2017 | Botes et al. |
| 9,650,653 B2 | 5/2017 | Pearlman et al. |
| 9,862,973 B2 | 1/2018 | Botes et al. |
| 9,920,339 B2 | 3/2018 | Kadi et al. |
| 10,072,150 B2 | 9/2018 | Conradie et al. |
| 10,196,657 B2 | 2/2019 | Pearlman et al. |
| 10,577,634 B2 | 3/2020 | Pearlman et al. |
| 10,975,363 B2 | 4/2021 | Foster et al. |
| 2002/0192786 A1 | 12/2002 | Yamada et al. |
| 2005/0181499 A1 | 8/2005 | Brahmbhatt |
| 2007/0264688 A1 | 11/2007 | Venter et al. |

(Continued)

FOREIGN PATENT DOCUMENTS

| | | |
|---|---|---|
| CN | 1735691 A | 2/2006 |
| CN | 102459579 A | 5/2012 |

(Continued)

OTHER PUBLICATIONS

Lu et al. "Studies in the production of branched-chain alcohols in engineered Ralstonia eutropha". Bioenergy and Biofuels. 2012, 96, pp. 283-297.*
Grousseau et al. Appl Microbiol Biotechnol, 2014, 98, pp. 4277-4290.*
Pohlmann et al. "Genome sequence of the bioplastic producing 'knallgas' bacterium Ralstonia eutropha H16". Natural Biotechnology, 2007, 25(4), 478, pp. 1-7.*
Pohlmann et al. ("Genome sequence of the bioplastic producing 'knallgas' bacterium Ralstonia eutropha H16". Natural Biotechnology, 2006, vol. 24, No. 10, pp. 1257-1262 inlcuidng supplementatry information.*
PTO STIC search in GenEmbl datase run on Jun. 27, 2022, pp. 1-6.*
Alagesan, S., et al., "13C-assisted metabolic flux analysis to investigate heterotrophic and mixotrophic metabolism in Cupriavidus necator H16", Metabolomics, 2018, vol. 14, Issue 9, pp. 9.

(Continued)

*Primary Examiner* — Vera Afremova

(57) ABSTRACT

Provided herein are methods for increasing the yield of an extracellular product synthesized by an organism cultured in a continuous aerobic fermentation system. The extracellular product yield is increased through the use of an organism modified to decreased production of polyhydroxyalkanoate, to increase production of the extracellular product, and to include promoters that can be inducible in response to nutrient limitation conditions. The extracellular product yield is also increased by operating the continuous fermentation system under particular nutrient limitation conditions. Also provided are non-naturally occurring organisms that have been modified for use with the provided methods, and extracellular products made using the provided methods.

16 Claims, 2 Drawing Sheets

Specification includes a Sequence Listing.

(56) References Cited

U.S. PATENT DOCUMENTS

| | | |
|---|---|---|
| 2007/0269862 A1 | 11/2007 | Glass et al. |
| 2010/0120104 A1 | 5/2010 | Reed |
| 2010/0167371 A1 | 7/2010 | Chotani et al. |
| 2011/0125118 A1 | 5/2011 | Lynch |
| 2011/0171702 A1 | 7/2011 | Reinecke et al. |
| 2012/0003706 A1 | 1/2012 | Hickey |
| 2012/0064622 A1 | 3/2012 | Fischer et al. |
| 2012/0295334 A1 | 11/2012 | Brahmbhatt |
| 2013/0034884 A1 | 2/2013 | Burgard et al. |
| 2013/0065285 A1 | 3/2013 | Sefton |
| 2013/0177957 A1 | 7/2013 | Du et al. |
| 2013/0189763 A1 | 7/2013 | Dalla-betta et al. |
| 2013/0323714 A1 | 12/2013 | Cheng et al. |
| 2014/0248687 A1 | 9/2014 | Kelly et al. |
| 2014/0330398 A1 | 11/2014 | Fan et al. |
| 2015/0132815 A1 | 5/2015 | Hickey |
| 2015/0315599 A1 | 11/2015 | Shetty et al. |
| 2016/0176813 A1 | 6/2016 | Valdez |
| 2017/0107474 A1 | 4/2017 | Farmer et al. |
| 2017/0159082 A1 | 6/2017 | Conradie et al. |
| 2017/0218406 A1 | 8/2017 | Conradie et al. |
| 2018/0023088 A1 | 1/2018 | Van Eck Conradie et al. |
| 2018/0023103 A1 | 1/2018 | Foster et al. |
| 2018/0023104 A1 | 1/2018 | Cartman et al. |
| 2018/0100160 A1 | 4/2018 | Bawdon et al. |
| 2018/0327705 A1 | 11/2018 | Matsuka et al. |
| 2019/0124947 A1* | 5/2019 | Pearlman ............... A23K 10/12 |
| 2019/0300838 A1 | 10/2019 | Smith et al. |
| 2019/0300839 A1 | 10/2019 | Smith et al. |
| 2019/0316072 A1 | 10/2019 | Smith et al. |
| 2019/0338320 A1 | 11/2019 | Foster et al. |
| 2019/0352682 A1 | 11/2019 | Foster et al. |
| 2019/0359957 A1 | 11/2019 | Foster et al. |

FOREIGN PATENT DOCUMENTS

| | | |
|---|---|---|
| CN | 106795537 A | 5/2017 |
| CN | 107849300 A | 3/2018 |
| EP | 0995490 A2 | 4/2000 |
| EP | 1728853 A1 | 12/2006 |
| EP | 1938892 A1 | 7/2008 |
| EP | 3399015 A1 | 11/2018 |
| JP | S49124358 A | 11/1974 |
| JP | H03127983 A | 5/1991 |
| JP | 2007185133 A | 7/2007 |
| JP | 2009225662 A | 10/2009 |
| JP | 2013179909 A | 9/2013 |
| RU | 2644344 C1 | 2/2018 |
| WO | 2008094282 A1 | 8/2008 |
| WO | 2010003007 A2 | 1/2010 |
| WO | 2010069313 A2 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2017115855 A1 | 7/2014 |
| WO | 2015032375 A1 | 3/2015 |
| WO | 2015117019 A1 | 8/2015 |
| WO | 2015149147 A1 | 10/2015 |
| WO | 2015195654 A1 | 12/2015 |
| WO | 2017165244 A1 | 9/2017 |
| WO | 2018005770 A2 | 1/2018 |
| WO | 2018022595 A1 | 2/2018 |
| WO | 2018022633 A1 | 2/2018 |
| WO | 2018106549 A1 | 6/2018 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A1 | 11/2019 |

OTHER PUBLICATIONS

Alagesan, S., et al., "Functional genetic elements for controlling gene expression in Cupriavidus necator H16", Applied and Environmental Microbiology, vol. 84, Oct. 2018 (Oct. 2018), pp. 1-17.

Anderson, A.J., et al., "Occurrence, metabolism, metabolic role, and industrial uses of bacterial polyhydroxyalkanoates", Microbiology Review, 1990, vol. 54, pp. 450-472.

Atlic et al., "Continuous Production of Poly([R]-3-Hydroxybutyrate) by Cupriavidus Necator in a Multistage Bioreactor Cascade", Appl Microbial Biotechnology, vol. 91, 2011, pp. 295-304.

Bramer, C.O., "The malate dehydrogenase of Ralstonia eutropha and functionality of the C(3)/C(4) metabolism in a Tn5-induced mdh mutant", FEMS Microbiol Letters, Jul. 2, 2002, vol. 212, Issue 2, pp. 159-164.

Brandt, U., et al., "Elevated poly(3-hydroxybutyrate) synthesis in mutants of Ralstonia eutropha HI6 defective in lipopolysaccharide biosynthesis" Applied Microbiology and Biotechnology, 2012, vol. 95, pp. 471-483.

Brigham, C.J., et al., "Correction for Whole-genome microarray and gene deletion studies reveal regulation of the polyhydroxyalkanoate production cycle by the stringent response in Ralstonia eutropha H16", Appl Environ Microbiol., 2017, vol. 83, Issue 15, pp. 1-2.

Brigham, C.J., et al., "Whole-genome microarray and gene deletion studies reveal regulation of the polyhydroxyalkanoate production cycle by the stringent response in Ralstonia eutropha HI6", Appl Environ Microbial., 2012, vol. 78, Issue 22, pp. 8033-8044.

Brown, D.R., et al., "Nitrogen stress response and stringent response are coupled in *Escherichia coli*", Nature Communications, 2014, vol. 5, 4115, pp. 8.

Bruland et al. "Unravelling the C3/C4 carbon metabolism in Ralstonia eutropha H16" Journal of Applied Microbiology 2010 109:79-90.

Chae, T.U., et al., "Metabolic engineering of *Escherichia coli* for the production of four-, five- and six-carbon lactarns Metabolic Engineering", Academic Press, US, vol. 41 ,Apr. 5, 2017, pp. 82-91.

Chakravarty, J., et al., "Solvent production by engineered Ralstonia eutropha: channeling carbon to biofuel", Applied Microbiology and Biotechnology, vol. 102, Apr. 29, 2018 (Apr. 29, 2018), pp. 5021-5031.

Chen, R., et al., "A highly active decarboxylating dehydrogenase with rationally inverted coenzyme specificity", PNAS, 1996, vol. 92, Issue 25, pp. 11666-11670.

Chen, R., et al. "Redesigning secondary structure to invert coenzyme specificity in isopropylmalate dehyrogenase" PNAS, 1996, vol. 93, pp. 12171-12176.

Choi, J.C., et al. "Modulation of 3-hydroxyvalerate molar fraction in poly(3-hydroxybutyrate-3- hydroxyvalerate) using Ralstonia eutropha transformant co-amplifying phbC and NADPH generation-related zwf genes", Enzyme and Microbial Technology, 2003, vol. 32, Issue 1, pp. 178-185.

Cramm, R. J. "Genomic view of energy metabolism in Ralstonia eutropha HI6", Journal of Molecular Microbiology and Biotechnology, 2009, vol. 16, pp. 38-52.

Darani, K.K., et al., "Simulation of bioreactors for poly(3-hydroxybutyrate) production from natural gas", Iranian Journal of Chemistry and Chemical Engineering, vol. 39, 2018, pp. 1-24.

Ding, H., et al., "Glycerol utilization by Rhizobium leguminosarum requires an ABC transporter and affects competition for nodulation", Microbiology, 2012, vol. 158, pp. 1369-1378.

Doberstein, C., et al., "Polythioester synthesis in Ralstonia eutropha H16: novel insights into 3,3'-thiodipropionic acid and 3,3'-dithiodipropionic acid catabolism" Journal of Biotechnology, 2014, vol. 184, pp. 187-198.

Eggers et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, No. 24, Dec. 2014, pp. 7702-7709.

Frng, Y., et al., "Tuning of acyl-ACP thioesterase activity directed for tailored fatty acid synthesis", Applied Microbiology And Biotechnology, Springer, De, vol. 102, No. 7 , Feb. 22, 2018, pp. 3173-3182.

(56) References Cited

OTHER PUBLICATIONS

Gao, C., et al. "Lactate utilization is regulated by the FadR-type regulator LidR in Pseudomonas aeruginosa", Journal of Bacteriology, 2012, vol. 194, pp. 2687-2692.
Girdhar, A., et al., "Process Parameters for Influencing Polyhyroxyalkanoate Producing Bacterial Factories: An Overview", Petroleum & Environmental Biotechnology, 2013, vol. 4, Issue 5, pp. 9.
Hanko, E.K.R., et al., "Characterisation of a 3-hydroxypropionic acid-inducible system from Pseudomonas putida for orthogonal gene expression control in *Escherichia coli* and Cupriavidus necator", Scientific Reports, vol. 7, 2017, pp. 1-12.
Hauryliuk, V., et al. "Recent functional insights into the role of (p)ppGpp in bacterial physiology", Nature Reviews Microbiology, 2015, vol. 13, pp. 298-309.
Haushalter, R.W., et al., "Production of Odd-Carbon Dicarboxylic Acids in *Escherichia coli* Using an Engineered Biotin-Fatty Acid Biosynthetic Pathway" Journal Of The American Chemical Society, vol. 139, No. 13 ,Mar. 21, 2017, pp. 4615-4618.
Horvat et al., "Mathematical Modelling and Process Optimization of a Continuous 5-Stage Bioreactor Cascade for11 Production of Poly[-(R)-3-Hydroxybutyrate] by Cupriavidus Necator", Bioprocess Biosyst Eng, vol. 36, 2013, pp. 1235-1250.
Hun-Suk Song et al: Enhanced isobutanolproduction from acetate by combinatorialoverexpression of acetyl-CoA synthetaseand anaplerotic enzymes in engineered*Escherichia coli*, Biotechnology And Bioengineering,vol. 115, May 2, 2018 (May 2, 2018), pp. 1971-1978.
Lenczak, J.L., et al., "High cell density strategy for poly(3-hydroxybutyrate) production by Cupriavidus necator", Brazilian Journal of Chemical Engineering, 2011, vol. 28, Issue 4, pp. 585-596.
Inoue, H., et al., "Biochemical and molecular characterization of the NAD(+)-dependent isocitrate dehydrogenase from the chemolithotrophAcidithiobacillus thiooxidans", FEMS Microbial Letters, 2002, vol. 214, Issue 1, pp. 127-132.
International Search Report and Written Opinion for International Application Serial No. PCT/US2019/025189, dated Jul. 2, 2019, pp. 12.
International Search Report and Written Opinion for International Application Serial No. PCT/US2019/025194, dated Aug. 22, 2019, pp. 24.
International Search Report and Written Opinion for International Application Serial No. PCT/US2019/025202, dated Jul. 30, 2019, pp. 15.
International Search Report and Written Opinion for International Application Serial No. PCT/US2019/025211, dated Jul. 29, 2019, pp. 16.
International Search Report and Written Opinion for International Application Serial No. PCT/US2019/025218, dated Sep. 5, 2019, pp. 17.
International Search Report and Written Opinion for International Application Serial No. PCT/US2019/029973 dated Jul. 23, 2019, dated Jul. 23, 2019, 5 pgs.
International Search Report and Written Opinion in PCT/US2019/029795 dated Jul. 11, 2019, pp. 10.
International Search Report and Written Opinion in PCT/US2019/029798 dated Sep. 12, 2019, p. 19.
International Search Report and Written Opinion in PCT/US2019/029817 dated Sep. 23, 2019.
International Search Report and Written Opinion in PCT/US2019/029827 dated Sep. 23, 2019.
International Search Report and Written Opinion in PCT/US2019/029956 dated Aug. 13, 2019.
Invitation to Pay Additional Fees and, Where Applicable, Protest Fee in PCT/082019/029798 dated Jul. 22, 2019.
Invitation to Pay Additional Fees and, WhereApplicable, Protest Fee in PCT/US2019/029817 dated Aug. 1, 2019.
Invitation to Pay Additional Fees and, WhereApplicable, Protest Fee in PCT/US2019/029827 dated Jul. 23, 2019.

Jhonson, A., et al., "An engineered constitutive promoter set with broad activity range for Cupriavidus necator H16", ACS Synthetic Biology, vol. 7, Jun. 27, 2018 (Jun. 27, 2018), pp. 1918-1928.
Joris, Beld, et al., "Evolution of acyl-ACP thioesterases and [beta]-ketoacyl-ACP synthases revealed by protein-protein interactions", Journal Of Applied Phycology, vol. 26, No. 4 ,Nov. 22, 2013, pp. 1619-1629.
Juengert, J.R, et al., "Absence of ppGpp Leads to Increased Mobilization of Intermediately Accumulated Poly(3-Hydroxybutyrate) in Ralstonia eutropha HI6" Applied and Environmental Microbiology, 2017, vol. 83, Issue 13, pp. e00755-17.
Justyna Mozejko-Ciesielska et al: "Bacterial polyhydroxyalkanoates: Still fabulous?", Microbiological Research, vol. 192, 2016, pp. 271-282.
Kaddor, C., et al., "Effects of homologous phosphoenolpyruvate-carbohydrate phosphotransf erase system proteins on carbohydrate uptake and poly(3-ydroxybutyrate) accumulation in Ralstonia eutropha HI6", Appl. Environ. Microbiol., 2011, vol. 77, pp. 3582-3590.
Kaddor, C., et al., "Implications of various phosphoenolpyruvate-carbohydrate phosphotransf erase system mutations on glycerol utilization and poly(3-hydroxybutyrate) accumulation in Ralstonia eutropha H16", AMB Express, 2011, vol. 1, pp. 16.
Byrd et al., "Bacterial Control of Agromyces Ramosus in Soil", Canadian Journal of Microbiology, vol. 31, No. 12, 1985, pp. 1157-1163.
Du et al., "E ffects of Environmental Conditions on Cell Growth and Poly-B-Hydroxybutyrate Accumulation in Alcaligenes Eutrophus", World Journal of Microbiology & Biotechnology, vol. 16, 2000, pp. 9-13.
Grousseau et al., "Isopropanol Production with Engineered Cupriavidus Necator as Bioproduction Platform", Appl. Microbiol. Biotechnol., vol. 98, No. 9, 2014, pp. 4277-4290.
Gyaneshwar et al., "Sulfur and Nitrogen Limitation in *Escherichia coli* K-12: Specific Homeostatic Responses", Journal of Bacteriology, vol. 187, No. 3, Feb. 2005, pp. 1074-1090.
Koller et al., "Potential and Prospects of Continuous Polyhydroxyalkanoate (PHA) Production", Bioengineering, May 29, 2015, pp. 94-121.
Lee et al., "Microbial Production of Ethanol from Acetate by Engineered Ralstonia Eutropha", Biotechnology and Bioprocess Engineering, vol. 21, 2016, pp. 402-407.
Lu et al., "Studies on the Production of Branched-chain Alcohols in Engineered Ralstonia Eutropha", Appl. Microbiol. Biotechnol., vol. 96, No. 1, 2012, 15 pages.
Makkar et al., "Cupriavidus Necator gen. nov., sp. nov .; a Nonobligate Bacterial Predator of Bacteria in Soil", International Journal of Systematic Bacteriology, vol. 37, No. 4, Oct. 1987, pp. 323-326.
Przybylski et al., "Synthesis of the Building Block 2-Hydroxyisobutyrate from Fructose and Butyrate by Cupriavidus Necator H16", Appl. Microbiol. Biotechnol., vol. 97, 2013, pp. 8875-8885.
Russell , "The Energy Spilling Reactions of Bacteria and Other Organisms", Journal of Molecular Microbiology Biotechnology, vol. 13, No. 1, 2007, pp. 1-11.
Schramke et al., "Revisiting Regulation of Potassium Homeostasis in *Escherichia coli*: The Connection to Phosphate Limitation", Wiley Microbiologyopen, vol. 6, No. 3, 2017, pp. 1-16.
Shang et al., "Poly(3-hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-1419.
Sillman et al., "Isolation of Nonobligate Bacterial Predators of Bacteria from Soil", Canadian Journal of Microbiology, vol. 32, No. 9, 1986, pp. 760-762.
Vollbrecht et al., "Excretion of Metabolites by Hydrogen Bacteria I. Autotrophic and Heterotrophic Fermentations", European journal of applied microbiology and biotechnology, vol. 6, Issue 2, 1978, pp. 145-155.
Vollbrecht et al., "Excretion of Metabolites by Hydrogen Bacteria II. Influences of Aeration, pH, Temperature, and Age of Cells", European Journal of Applied Microbiology and Biotechnology, vol. 6, Issue 2, 1978, pp. 157-166.
Vollbrecht et al., "Excretion of Metabolites by Hydrogen Bacteria IV. Respiration Rate-dependent Formation of Primary Metabolites

(56) References Cited

OTHER PUBLICATIONS and of Poly-3-Hydroxybutanoate", European Journal of Applied Microbiology and Biotechnology, vol. 7, Issue 3, 1979, pp. 267-276.
Wang et al., "Poly(3-Hydroxybutyrate) Production with High Productivity and High Polymer Content by a Fed-Batch Culture of Alcaligenes latus under Nitrogen Limitation", Applied and Environmental Microbiology, vol. 63, No. 9, Sep. 1997, pp. 3703-3706.
Weiden et al., "Cation Transport in *Escherichia coli* Vii. Potassium Requirement for Phosphate Uptake", The Journal of General Physiology, vol. 50, No. 6, 1967, pp. 1641-1661.
Youngquist et al., "Functional Genomics Analysis of Free Fatty Acid Production under Continuous Phosphate Limiting Conditions", J. Ind. Microbiol. Biotechnol., vol. 44, May 2017, pp. 759-772.
Zeph et al., "Gram-Negative Versus Gram-Positive (Actinomycete) Nonobligate Bacterial Predators of Bacteria in Soil", Applied Environmental Microbiology, vol. 52, No. 4, Oct. 1986, pp. 819-823.
Karstens, K., et al., "Phosphotransferase protein EIIANtr interacts with SpoT, a key enzyme of the stringent response, in Ralstonia eutropha HI6", Microbiology, 2014, vol. 160, pp. 711-722.
Katalin Kovacs et al: Metabolic engineering of Cupriavidus necator H16 for the sustainable production of C3 and C5 monomers and polymers, Clnet Conference 4, Jan. 20-23, 2019 Conference paper (Abstract), 2019, p. 26.
Kazakov, A.E., et al., "Comparative genomics of regulation of fatty acid and branched-chain amino acid utilization in proteobacteria", Journal of Bacteriology, 2009, vol. 191, pp. 52-64.
Kim et al. "Effect of overexpression of Actinobacillus succinogenes phosphoenolpyruvate carboxykinase on succinate production in *Escherichia coli*" Applied and Environmental Microbiology, 2004, vol. 70, Issue 2, pp. 1238-1241.
Kluge, J., et al., "Inducible promoters and functional genomic approaches for the genetic engineering of filamentous fungi", Applied Microbiology and Iotechnology, vol. 102, Jun. 2, 2018 (Jun. 2, 2018), pp. 6357-6372.
Koller, M., "A review on established and emerging fermentation schemes for microbial production of polyhydroxyalkanoate (PHA) biopolyesters", Fermentation, vol. 4, Apr. 23, 2018 (Apr. 23, 2018), pp. 1-30.
Koller, M., et al., "Continuous production mode as a viable process-engineering tool for efficient poly (hydroxyalkanoate) (PHA) bio-production", Chemical and Biochemical Product Engineering, vol. 28, Issue 1, 2014, pp. 65-77.
Krausse et al., "Essential role of the hprK gene inRalstonia eutropha HI6", J Mol Microbiol Biotechnol, 2009, vol. 17, pp. 146-152.
Kunasundari et al., "Revisiting the Single Cell Protein Application of Cupriavidus Necator H16 and Recovering Bioplastic Granules Simultaneously", Plos One, vol. 8, No. 10, Oct. 2013, 15 pages.
Lardi, M., et al., "o54-Dependent Response to Nitrogen Limitation and Virulence in Burkholderia cenocepacia Strain H111" Appl. Environ. Microbiol., 2015, vol. 81, Issue 12, pp. 4077-4089.
Lee, J.N., et al., "Metabolic Engineering of Pentose Phosphate Pathway in Ralsonia eutropha for Enhanced Biosynthesis of Poly- -hydroxybutyrate", Biotechnology Progress, 2003, vol. 19, Issue 5, pp. 1444-1449.
Lee, et al., "Regulation of poly- -hydroxybutyrate biosynthesis by nicotinamide nucleotide in Alcaligene eutrophus" FEMS Microbiological letters, 1995, vol. 131, pp. 35-39.
Leyn et al., "Control of proteobacterial centralcarbon metabolism by the HexR transcriptionalregulator: a case study in Shewanella oneidensis", Journal of Biological Chemistry, 2011, vol. 286, Issue 41, pp. 35782-35794.
Leyn, S.A., et al. "Comparative genomics and evolution of transcriptional regulons in Proteobacteria", Microbial Genomics, 2016, pp. 1-15.
Li, Z.J., et al., "Overexpression of NAD kinase in recombinant *Escherichia coli* harboring the phbCAB operon improves poly(3-hydroxybutyrate) production", Appl Microbial Biotechnol., 2009, vol. 83, Issue 5, pp. 939-947.
Liu, X., et al., "Comparative analysis of genes frequently regulated by drugs based on connectivity map transcriptome data" PLoS One, 2017, vol. 12, Issue 6, e0179037.
Marc, J., et al., "Over expression of GroESL in Cupriavidus necator for heterotrophic and autotrophic isopropanol production", Metabolic Engineering, vol. 42, 2017, pp. 74-84.
March, J.C., et al., "Expression of an anaplerotic enzyme, pyruvate carboxylase, improves recombinant protein production in *Escherichia coli*" Applied and Environmental Microbiology, 2002, vol. 68, Issue 11, pp. 5620-5624.
Martin, Koller, et al., "Continuous production mode as a viable process-engineering tool for efficient poly (hydroxyalkanoate) (PHA) bio-production", Chemical And Biochemical Engineering Quarterly, vol. 28, XP002792820 ,2014, pp. 65-77.
McKinlay, J.B., et al., "Carbon dioxide fixation as a central redox cofactor recycling mechanism in bacteria" PNAS, 2010, vol. 107, Issue 26, pp. 11669-11675.
Meng, J., et al. "High-yield anaerobic succinate production by strategically regulating multiple metabolic pathways based on stoichiometric maximumin *Escherichia coli*" Microbial Cell Factories, vol. 15, 2016, pp. 13.
Montiel-Jarillo, G., et al., "Enrichment of a mixed microbial culture for polyhydroxyalkanoates production: Effect of pH and N and P concentrations", Science of the Total Environment, vol. 583, 2017, pp. 300-307.
Nguyen, C., et al., "Trapping the dynamic acyl carrier protein in fatty acid biosynthesis", Nature, vol. 505, No. 7483 ,Dec. 22, 2013, pp. 427-431.
Obruca, S., et al. "Application of random mutagenesis to enhance the production of polyhydroxyalkanoates by Cupriavidus necator H16 on waste frying oil", World J Microbiol Biotechnol, 2013, vol. 29, pp. 2417-2428.
Olaya-Abril et al., "Poly(3-hydroxybutyrate) hyperproduction by a global nitrogen regulator NtrB mutant strain of Paracoccus denitrificans PD1222", Fems Microbiology Letters, 2008, vol. 365:fnx251, pp. 8.
Orita, L., et al., "Identification of mutation points in Cupriavidus necator NCIMB 11599 and genetic reconstitution of glucose-utilization ability in wild strain H16 for polyhydroxyalkanoate production" Journal of Bioscience and Bioengineering, 2012, vol. 113, Issue 1, pp. 63-69.
Papagiani, M., "Recent advances in engineering the central carbon metabolism of industrially important bacteria", Microbial Cell Factories, 2012, vol. 11, pp. 13.
Park, J-S., et al., "Metabolic Characteristics of Isocitrate Dehydrogenase Leaky Mutant of Alcaligene eutrophus and Its Utilization for Poly-Hydroxybutyrate Production" Journal of Fermentation and Bioengineering, 1996, vol. 81, Issue 3, pp. 197-205.
Park, S., et al., "Oxaloacetate and malate production in engineered *Escherichia coli* by expression of codon-optimized phosphoenolpyruvate carboxylase2 gene from Dunaliella salina", Bioprocess Biosyst Eng., 2013, vol. 36, Issue 1, pp. 127-131.
Persuhn, D.C., et al. "The transcriptional activator NtrC controls the expression and activity of glutamine synthetase in Herbaspirillum seropedicae" FEMS Microbiology Letters, 2000, vol. 192, pp. 217-221.
Pohlmann, A., et al., "Genome sequence of the bioplastic-producing "Knallgas" bacterium Ralsonia eutropha HI6" Nature Biotechnology, 2007, vol. 24, No. 10, pp. 1257-1262.
Qi et al., "Model-driven redox pathway manipulation for improved isobutanol production in Bacillus subtilis complemented with experimental validation and metabolic profiling analysis" PLoS ONE, 2014, vol. 9, Issue 4, : e93815, pp. 1-11.
Raberg, M., "Ralstoni a eutropha H16 in progress: applications beside PHAs and establishment as production platform by advanced genetic tools", Critical Reviews in Biotechnology, vol. 38, Dec. 12, 2017 (Dec. 12, 2017), pp. 494-510.
Raberg, M., et al., "A closer look on the polyhydroxybutyrate-(PHB-) negative phenotype of Ralstonia eutropha PHB-4" PLoS One, 2014, vol. 9, Issue 5, pp. 11.
Rosa, L.T., et al., "Tripartite ATP-Independent Periplasmic (TRAP) Transporters and Tripartite Tricarboxylate Transporters (TTT): From Uptake to Pathogenicity", Frontiers in Microbiology, 2018, vol. 8, pp. 16.

(56) References Cited

OTHER PUBLICATIONS

Sacamboio, E.N.M., et al. "The transcriptional regulator NtrC controls glucose-6-phosphate dehydrogenase expression and polyhydroxybutyrate synthesis through NADPH availability in Herbaspirillum seropedicae" Scientific Reports, 2017, vol. 7, Article No. 13546, pp. 1-12.

Sanchez, A.M., et al., "Effect of overexpression of a soluble pyridine nucleotide transhydrogenase (UdhA) on the production of poly(3-hydroxybutyrate) in *Escherichia coli*" Biotechnol Prog., 2006, vol. 22, Issue 2, pp. 420-425.

Saur, U., et al.,"The PEP-pyruvate-oxaloacetate node as the switch point for carbon flux distribution in bacteria", FEMS Microbiology Reviews, 2005, vol. 29, Issue 4, pp. 765-794.

Schlegel, H.G., et al., "Formation of the Dehydroganses for Lactate, Ethanol and Butanediol in the Strictly Aerobi Bacterium Alcaligene eutrophus" Microbiology, 1980, vol. 117, pp. 475-481.

Schobert, P., et al., "Unusual C3 and C4 metabolism in the chemoautotroph Alcaligenes eutrophus" Journal of Bacterialogy, 1984, vol. 159, Issue 1, pp. 167-172.

Schwartz, E., et al., "A proteomic view of the facultatively chemolithoautotrophic lifestyle of Ralstonia eutropha H16" Proteomics, 2009, vol. 9, Issue 22, pp. 5132-5142.

Segura, D., et al., "Inactivation of pycA, encoding pyruvate carboxylase activity, increases polybeta-hydroxybutyrate accumulation in Azotobacter vinelandii on solid medium" Appl Microbial Biotechnol, 2004, pp. 65, Issue 4, pp. 414-418.

Sekar, B.S., et al., "Co-production of hydrogen and ethanol from glucose in *Escherichia coli* by activation of pentose-phosphate pathway through deletion of phosphoglucose somerase (pgi) and overexpression of glucose-6-phosphate dehydrogenase (zwf) and 6-phosphogluconate dehydrogenase ( gnd)", Biotechnology for Biofuels, 2017, vol. 10, 85, pp. 12.

Shively, J.M., et al., "Something From Almost Nothing: Carbon Dioxide Fixation In Chemoautotrophs", Annu. Rev. Microbiol., vol. 52, 1998, pp. 191-230.

Silva, F., et al., "Impact of nitrogen feeding regulation on polyhydroxyalkanoates production by mixed microbial cultures", New Biotechnology, vol. 37, 2017, pp. 90-98.

Steinbuchel, A., et al., "A multifunctional fermentative alcohol dehydrogenase from the strict aerobe Alcaligenes eutrophus: purification and properties" Eur J Biochem, 1984, vol. 141, Issue 3, pp. 555-564.

Stokke, R., et al., "Biochemical characterization of isocitrate dehydrogenase from Methylococcus capsulatus reveals a unique NAD+-dependent homotetrameric enzyme" Arch Microbiol., 2007, vol. 187, Issue 5, pp. 361-370.

Sun, J., et al., "Involvement of glnB, glnZ, and glnD genes in the regulation of poly-3-hydroxybutyrate biosynthesis by ammonia in Azospirillum brasilense Sp7", Appl. Environ. Microbiol, 2002, vol. 68, Issue 2, pp. 985-988.

Sun, J., et al., "The ntrB and ntrC genes are involved in the regulation of poly-3-hydroxybutyrate biosynthesis by ammonia in Azospirillum brasilense Sp7", Appl. Environ. Microbiol., 2000, vol. 66, Issue 1, pp. 113-117.

Tan, Z., et al. "Activating phosphoenolpyruvate carboxylase and phosphoenolpyruvate carboxykinase in combination for improvement of succinate production" Appl. Environ. Microbiol, 2013, vol. 79, Issue 16, pp. 4838-4844.

Tanaka, K, et al., Production Of Poly (D-3-Hydroxybutyrate) From CO2, H2, And O2 By High Cell Density Autotropic Cultivation Of Alcaligenes Eutrophus Biotechnology And Bioengineering, Wiley, vol. 45, No. 3, (Feb. 5, 1995), XP000489583 ,Feb. 5, 1995, 268-275.

Valderrama, J.A., et al., "AccR is a master regulator involved in carbon catabolite repression of the anaerobic catabolism of aromatic compounds in Azoarcus sp. CIB" Journal of Biological Chemistry, 2014, vol. 289, Issue 4, pp. 1892-1904.

Vemuri, G.N., et al., "Physiological response of central metabolism in *Escherichia coli* to deletion of pyruvate oxidase and introduction of heterologous pyruvate carboxylase" Biotechnology and Bioengineering, 2005, vol. 90, Issue 1 pp. 64-76.

Vollbrecht, D., et al., "Excretion of Metabolites by hydrogen Bacteria III. D(-)-3-hydroxybutanoate", European J. Appl. Microbiol. Biotechnol., 1979, vol. 7, pp. 259-266.

Volodina, E., et al., "Characterization of propionate CoA-transferase from Ralstonia eutropha H16", Appl Microbial Biotechnol., 2014, vol. 98, Issue 8, pp. 3579-3589.

Wang, R., et al., "Isocitrate dehydrogenase from *Streptococcus mutans*: biochemical properties and evaluation of a putative phosphorylation site at Ser102" PLoS One, 2013, vol. 8, Issue 3, e58918.

Weinberg, Z., et al. "Identification of 22 candidate structured RNAs in bacteria using the Cmfinder comparative genomics pipeline" Nucleic Acids Research, 2007, vol. 35, pp. 4809-4819.

Winnen, B., et al., "The tripartite tricarboxylate transporter (TTT) family" Res. Microbial., 2003, vol. 154, Issue 7, pp. 457-465.

Wu, M-C., et al., "A Novel Type II NAD+-Specific Isocitrate Dehydrogenase from the Marine Bacterium Congregibacter litoralis KT71" PLoS One., 2015, vol. 10, Issue 5, pp. 1-17.

Zhu, J., et al., "Factors for promoting polyhydroxyalkanoate (PHA) synthesis in bio-nutrient-removal and recovery system", 4th International Conference on nvironmental Systems Research (ICESR 2017) Conference paper, 2018, pp. 1-4.

Ziesack, M., et al., "Chimeric Fatty Acyl-Acyl Carrier Protein Thioesterases Provide Mechanistic Insight into Enzyme Specificity and Expression", Applied And Environmental Microbiology, vol. 84, No. 10, Mar. 16, 2018, pp. 12.

Kizer L et al. Application of Functional Genomics to Pathway Optimization for Increased Isoprenoid Production. Applied andEnvironmental Microbiology. 2008. vol. 74, No. 10. p. 3229-3241. (Year. 2008).

Non-final office action received for U.S. Appl. No. 16/398,351, dated Feb. 1, 2021, 24 pages.

Non-final office action received for U.S. Appl. No. 16/398,401, dated Feb. 16, 2021, 29 pages.

Non-final office action received for U.S. Appl. No. 16/398,365, dated Jan. 25, 2021, 10 pages.

Prather KLJ et al. De nova biosynthetic pathways: Rational design of microbial chemical factories. Current Opinion in Biotechnology, 2008. 19:468-47 4 (Year: 2008).

Singh RK et al. Protein Engineering Approaches in the Post-Genomic Era. 2017. Current Protein and Peptide Science. 18, 1-11. (Year: 2017).

Uniprot database, entry A0A0U2WHG0, Mar. 2016.

Zhang M et al. Propagated Perturbations from a Peripheral Mutation Show Interactions Supporting WW Domain Thermostablity, 2018, Structure. 26, 1474-1485. (Year: 2018).

Devos et al., "Practical Limits of Function Prediction", PROTEINS: Structure, Function and Genetics, vol. 41, pp. 98-107 (2000).

Kisselev, "Polypeptide Release Factors in Prokaryotes and Eukaryotes: Same Function, Different Structure", Structure, vol. 10, pp. 8-9 (2002).

Non-Final office action received for U.S. Appl. No. 16/398,384, dated Oct. 23, 2020, 13 pages.

Whisstock et al., "Prediction of protein function from protein sequence and structure", Quarterly Reviews of BioPhysics, vol. 36, Issue 3, pp. 307-340 (2003).

Witkowski et al., "Conversion of β-Ketoacyl Synthase to a Malonyl Decarboxylase by Replacement of the Active-Site Cysteine with Glutamine", Biochemistry, vol. 38, pp. 11643-11650 (1999).

Cavalheiro, J., et al., "Poly(3-hydroxybutyrate) production by Cupriavidus necator using waste glycerol", Process Biochemistry, vol. 44, Issue 5, 2009, pp. 509-515.

"Aminotransferase class III-fold pyridoxal phosphate-dependent enzyme [*Aquitalea denitrificans*]", NCBI Reference Sequence: WP_159877958.1, Jan. 19, 2020, 1 page.

"Aminotransferase class III-fold pyridoxal phosphate-dependent enzyme [*Aquitalea sp. LB_tupeE*]", NCBI Reference Sequence: WP_178973970.1, Jul. 11, 2020, 1 page.

"Aminotransferase class III-fold pyridoxal phosphate-dependent enzyme [*Chromobacterium haemolyticum*]", NCBI Reference Sequence: WP_166453011.1, Apr. 6, 2020, 1 page.

(56) References Cited

OTHER PUBLICATIONS

"Aminotransferase class III-fold pyridoxal phosphate-dependent enzyme [*Chromobacterium vaccinii*]", NCBI Reference Sequence: WP_166440807.1, Apr. 6, 2020, 1 page.
"Aminotransferase class III-fold pyridoxal phosphate-dependent enzyme [*Crenobacter sedimenti*]", NCBI Reference Sequence: WP_163315775.1, Apr. 6, 2020, 1 page.
"Aminotransferase class III-fold pyridoxal phosphate-dependent enzyme [*Neisseriaceae bacterium*B2N2-7]", GenBank: MXR37125.1, Jan. 6, 2020, 2 pages.
"Aminotransferase class III-fold pyridoxal phosphate-dependent enzyme [*Paludibacterium paludis*]", NCBI Reference Sequence: WP_189532963.1, Sep. 28, 2020, 1 page.
"Aminotransferase class III-fold pyridoxal phosphate-dependent enzyme [*Paludibacterium* sp. dN 18-1]", GenBank: MTD33855.1, Nov. 24, 2019, 1 page.
"Aminotransferase class III-fold pyridoxal phosphate-dependent enzyme [*Vogesella alkaliphila*]", NCBI Reference Sequence: WP_189374996.1, Sep. 28, 2020, 1 page.
"Aminotransferase class III-fold pyridoxal phosphate-dependent enzyme [*Vogesella fluminis*]", NCBI Reference Sequence: WP_189352298.1, Sep. 28, 2020, 1 page.
"Aminotransferase class III-fold pyridoxal phosphate-dependent enzyme [*Vogesella oryzae*]", NCBI Reference Sequence: WP_174874069.1, Jun. 22, 2020, 1 page.
"Aspartate aminotransferase family protein [*Aquitalea magnusonii*]", NCBI Reference Sequence: WP_059287319.1, Dec. 31, 2020. 1 page.
"Aspartate aminotransferase family protein [*Aquitalea magnusonii*]", NCBI Reference Sequence: WP_089085350.1, Jul. 15, 2017, 1 page.
"Aspartate aminotransferase family protein [*Aquitalea* sp. FJL05]", NCBI Reference Sequence: WP_124643387.1, Apr. 12, 2019, 1 page.
"Aspartate aminotransferase family protein [*Aquitalea* sp. THG-DN7.12]", NCBI Reference Sequence: WP_137009623.1, Oct. 16, 2019, 1 page.
"Aspartate aminotransferase family protein [*Chromobacterium amazonense*]", NCBI Reference Sequence: WP_106076402.1, Mar. 16, 2018, 1 page.
"Aspartate aminotransferase family protein [*Chromobacterium haemolyticum*]", GenBank: OQS32233.1, Apr. 6, 2017, 2 pages.
"Aspartate aminotransferase family protein [*Chromobacterium haemolyticum*]", GenBank: OQS37730.1, Apr. 6, 2017, 2 pages.
"Aspartate aminotransferase family protein [*Chromobacterium haemolyticum*]", NCBI Reference Sequence: WP_043593957.1, Apr. 15, 2016, 1 page.
"Aspartate aminotransferase family protein [*Chromobacterium haemolyticum*]", NCBI Reference Sequence: WP_081556739.1, Apr. 8, 2017, 1 page.
"Aspartate aminotransferase family protein [*Chromobacterium haemolyticum*]", NCBI Reference Sequence: WP_081576047.1, Apr. 8, 2017, 1 page.
"Aspartate aminotransferase family protein [*Chromobacterium haemolyticum*]", NCBI Reference Sequence: WP_161523523.1, Oct. 5, 2020, 1 page.
"Aspartate aminotransferase family protein [*Chromobacterium paludis*]", NCBI Reference Sequence: WP_149295777.1, Oct. 5, 2020, 1 page.
"Aspartate aminotransferase family protein [*Chromobacterium phragmitis*]", NCBI Reference Sequence: WP_114062556.1, Dec. 20, 2020.
"Aspartate aminotransferase family protein [*Chromobacterium* sp. ATCC 53434]", NCBI Reference Sequence: WP_101708025.1, Jan. 10, 2018.
"Aspartate aminotransferase family protein [*Chromobacterium* sp. LK11]", NCBI Reference Sequence: WP_048412320.1, Apr. 15, 2016, 1 page.
"Aspartate aminotransferase family protein [*Chromobacterium* sp. LK1]", NCBI Reference Sequence: WP_048411976.1, Apr. 15, 2016, 1 page.
"Aspartate aminotransferase family protein [*Chromobacterium* sp. MWU13-2610]", NCBI Reference Sequence: WP_103321487.1, Jan. 31, 2018, 1 page.
"Aspartate aminotransferase family protein [*Chromobacterium* sp. MWU14-2602]", NCBI Reference Sequence: WP_103903523.1, Feb. 10, 2018, 1 page.
"Aspartate aminotransferase family protein [*Chromobacterium* sp. Panama]", NCBI Reference Sequence: WP_107799474.1, Apr. 25, 2018, 1 page.
"Aspartate aminotransferase family protein [Chromobacterium sphagni]", NCBI Reference Sequence: WP_071116856.1, Aug. 23, 2017, 1 page.
"Aspartate aminotransferase family protein [*Chromobacterium subtsugae*]", NCBI Reference Sequence: WP_047237256.1, Mar. 20, 2018, 1 page.
"Aspartate aminotransferase family protein [*Chromobacterium subtsugae*]", NCBI Reference Sequence: WP_047243213.1, Apr. 15, 2016, 1 page.
"Aspartate aminotransferase family protein [*Chromobacterium subtsugae*]", NCBI Reference Sequence: WP_047257673.1, Apr. 15, 2016, 1 page.
"Aspartate aminotransferase family protein [*Chromobacterium vaccinii*]", NCBI Reference Sequence: WP_046156378.1, Oct. 25, 2019, 1 page.
"Aspartate aminotransferase family protein [*Chromobacterium vaccinii*]", NCBI Reference Sequence: WP_104946997.1, Mar. 4, 2018, 1 page.
"Aspartate aminotransferase family protein [*Chromobacterium violaceum*]", NCBI Reference Sequence: WP_011135573.1, Jul. 28, 2019, 1 page.
"Aspartate aminotransferase family protein [*Chromobacterium violaceum*]", NCBI Reference Sequence: WP_048405256.1, Apr. 15, 2016, 1 page.
"Aspartate aminotransferase family protein [*Chromobacterium violaceum*]", NCBI Reference Sequence: WP_081573061.1, Apr. 8, 2017, 1 page.
"Aspartate aminotransferase family protein [*Chromobacterium violaceum*]", NCBI Reference Sequence: WP_152637556.1, Oct. 31, 2019, 1 page.
"Aspartate aminotransferase family protein [*Crenobacter* sp. GY 70310]", NCBI Reference Sequence: WP_136552942.1, Oct. 16, 2019, 1 page.
"Aspartate aminotransferase family protein [*Gulbenkiania indica*]", NCBI Reference Sequence: WP_055434103.1, May 14, 2017, 1 page.
"Aspartate aminotransferase family protein [*Gulbenkiania mobilis*]", NCBI Reference Sequence: WP_054286466.1, May 14, 2017, 1 page.
"Aspartate aminotransferase family protein [*Paludibacterium purpuratum*]", NCBI Reference Sequence: WP_133682408.1, May 12, 2019, 1 page.
"Aspartate aminotransferase family protein [*Paludibacterium yongneupense*]", NCBI Reference Sequence: WP_028535161.1, Apr. 15, 2016, 2 pages.
"Aspartate aminotransferase family protein [*Pseudogulbenkiania ferrooxidans*]", NCBI Reference Sequence: WP_008952788.1, Apr. 15, 2016, 2 pages.
"Aspartate aminotransferase family protein [*Pseudogulbenkiania ferrooxidans*]", NCBI Reference Sequence: WP_021478068.1, Apr. 15, 2016, 1 page.
"Aspartate aminotransferase family protein [*Pseudogulbenkiania* sp. MAI-1]", NCBI Reference Sequence: WP_024302818.1, Apr. 15, 2016, 2 pages.
"Aspartate aminotransferase family protein [*Pseudogulbenkiania* sp. NH8B]", NCBI Reference Sequence: WP_014087389.1, Apr. 15, 2016, 2 pages.
"Aspartate aminotransferase family protein [*Pseudogulbenkiania subflava*]", NCBI Reference Sequence: WP_085275708.1, Apr. 22, 2017, 1 page.
"Aspartate aminotransferase family protein [*Rhodobacteraceae bacterium* CH30]", GenBank: RQW28969.1, Dec. 2, 2018, 2 pages.

(56) References Cited

OTHER PUBLICATIONS

"Aspartate aminotransferase family protein [*Vogesella indigofera*]", NCBI Reference Sequence: WP_120809711.1, Nov. 4, 2018, 1 page.
"Aspartate aminotransferase family protein [*Vogesella mureinivorans*]", NCBI Reference Sequence: WP_147694092.1, Oct. 5, 2020, 1 page.
"Aspartate aminotransferase family protein [*Vogesella perlucida*]", NCBI Reference Sequence: WP_147687830.1, Oct. 5, 2020, 1 page.
"Aspartate aminotransferase family protein [*Vogesella* sp. EB]", NCBI Reference Sequence: WP_047966302.1, Apr. 15, 2016, 1 page.
"Aspartate aminotransferase family protein [*Vogesella* sp. LIG4]", NCBI Reference Sequence: WP_088967522.1, Jul. 11, 2017, 1 page.
"Aspartate aminotransferase family protein [*Vogesella urethralis*]", NCBI Reference Sequence: WP_144371715.1, Oct. 5, 2020, 1 page.
"Aspartate aminotransferase family protein [*Xenophilus* sp. AP218F]", NCBI Reference Sequence: WP_088737038.1, Jul. 3, 2017, 1 page.
"Crystal structure of the omega transaminase from Chromobacterium violaceum in complex with PMP", PDB:5S4G_A, Dec. 1, 2020, 2 pages.
"Multispecies: aspartate aminotransferase family protein [*Aquitalea*]", NCBI Reference Sequence: WP_045848621.1, Apr. 15, 2016, 1 page.
"Multispecies: aspartate aminotransferase family protein [*Aquitalea*]", NCBI Reference Sequence: WP_103523625.1, Aug. 6, 2020, 1 page.
"Multispecies: aspartate aminotransferase family protein [*Chromobacterium*]", NCBI Reference Sequence: WP_019104435.1, Apr. 18, 2017, 1 page.
"Multispecies: aspartate aminotransferase family protein [*Chromobacterium*]", NCBI Reference Sequence: WP_043572477.1, Apr. 15, 2016, 1 page.
"Multispecies: aspartate aminotransferase family protein [*Chromobacterium*]", NCBI Reference Sequence: WP_043629242.1, Oct. 31, 2016, 1 page.
"Multispecies: aspartate aminotransferase family protein [*Chromobacterium*]", WP_043638691.1, Nov. 11, 2020, 1 page.
"Multispecies: aspartate aminotransferase family protein [*Microvirgula*]", NCBI Reference Sequence: WP_028498438.1, Jul. 14, 2018, 1 page.
U.S. Appl. No. 16/372,072, Corrected Notice of Allowability dated Jan. 26, 2021, 2 pages.
U.S. Appl. No. 16/372,072, Notice of Allowance dated Jul. 17, 2020, 11 pages.
U.S. Appl. No. 16/372,072, Notice of Allowance dated Dec. 16, 2020, 9 pages.
U.S. Appl. No. 16/372,072, Preliminary Amendment filed Jul. 30, 2019, 5 pages.
U.S. Appl. No. 16/372,072, Preliminary Amendment filed Aug. 14, 2019, 5 pages.
U.S. Appl. No. 16/372,072, Response filed Feb. 11, 2020 to Restriction Requirement dated Dec. 11, 2019, 7 pages.
U.S. Appl. No. 16/372,072, Response filed Jun. 8, 2020 to Non Final Office Action dated Mar. 6, 2020, 11 pages.
U.S. Appl. No. 16/372,072, Restriction Requirement dated Dec. 11, 2019, 9 pages.
U.S. Appl. No. 16/372,083, Preliminary Amendment filed Jul. 30, 2019, 4 pages.
U.S. Appl. No. 16/372,083, Response filed Apr. 12, 2021 to Restriction Requirement dated Mar. 8, 2021, 8 pages.
U.S. Appl. No. 16/372,083, Response filed Dec. 18, 2020 to Restriction Requirement dated Oct. 19, 2020, 7 pages.
U.S. Appl. No. 16/372,083, Restriction Requirement dated Mar. 8, 2021, 6 pages.
U.S. Appl. No. 16/372,083, Restriction Requirement dated Oct. 19, 2020, 8 pages.
U.S. Appl. No. 16/372,092, Non Final Office Action dated Mar. 4, 2021, 9 pages.
U.S. Appl. No. 16/372,092, Response filed Jun. 2, 2021 to Non Final Office Action dated Mar. 4, 2021, 11 pgs.
U.S. Appl. No. 16/372,092, Response filed Dec. 17, 2020 to Restriction Requirement dated Oct. 21, 2020, 6 pages.
U.S. Appl. No. 16/372,092, Restriction Requirement dated Oct. 21, 2020, 7 pages.
U.S. Appl. No. 16/372,099, Non Final Office Action dated Jul. 9, 2021, 14 pages.
U.S. Appl. No. 16/372,099, Response filed May 18, 2021 to Restriction Requirement dated Mar. 19, 2021, 6 pages.
U.S. Appl. No. 16/372,099, Restriction Requirement dated Mar. 19, 2021, 6 pages.
U.S. Appl. No. 16/398,351, Non Final Office Action dated Feb. 1, 2021, 24 pages.
U.S. Appl. No. 16/398,365, Non Final Office Action dated Jan. 25, 2021, 10 pages.
U.S. Appl. No. 16/398,401, Non Final Office Action dated Feb. 16, 2021, 29 pages.
U.S. Appl. No. 16/399,145, Advisory Action dated Feb. 1, 2021, 4 pages.
U.S. Appl. No. 16/399,145, Final Office Action dated Dec. 4, 2020, 17 pages.
U.S. Appl. No. 16/399,145, Non Final Office Action dated Jun. 17, 2021, 20 pages.
U.S. Appl. No. 16/399,145, Response filed Jan. 25, 2021 to Final Office Action dated Dec. 4, 2020, 12 pages.
U.S. Appl. No. 16/399,145, Response filed Jun. 3, 2020 to Restriction Requirement dated Apr. 17, 2020, 7 pages.
U.S. Appl. No. 16/399,145, Response filed Nov. 6, 2020 to Non Final Office Action dated Aug. 12, 2020, 12 pages.
U.S. Appl. No. 16/399,145, Restriction Requirement dated Apr. 17, 2020, 9 pages.
U.S. Appl. No. 16/399,155, Advisory Action dated Jun. 1, 2020, 3 pages.
U.S. Appl. No. 16/399,155, Final Office Action dated Mar. 5, 2020, 23 pages.
U.S. Appl. No. 16/399,155, Final Office Action dated Jul. 28, 2021, 14 Pages.
U.S. Appl. No. 16/399,155, Non Final Office Action dated Feb. 16, 2021, 17 pages.
U.S. Appl. No. 16/399,155, Response filed May 5, 2020 to Final Office Action dated Mar. 5, 2020, 12 pages.
U.S. Appl. No. 16/399,155, Response filed May 14, 2021 to Non Final Office Action dated Feb. 16, 2021, 11 pages.
U.S. Appl. No. 16/399,155, Response filed Jun. 5, 2020 to Advisory Action dated Jun. 1, 2020, 13 pages.
U.S. Appl. No. 16/399,155, Response filed Jun. 5, 2020 to Final Office Action dated Mar. 5, 2020, 13 pages.
Brigham, C.J., et al., "Engineering Ralstonia eutropha for Production of Isobutanol from C02, H2 and 02", AdvancedBiofuels and Bioproducts, (2013) Chapter 39, pp. 1065-1090.
Cupriavidus necator, Wikipedia, Retrieved from Internet URL: https://en.wikipedia.org/wiki/Cupriavidus_necator#:-:text= Cupriavidus%20necator"/o20is%20a%20hydrogen,a%20source% 20of"/o20energy%20C., Feb. 25, 2021, 07 Pages.
Database UniProt [Online] Mar. 15, 2017 , "RecName: Full= Thiopurine S-methyltransferase {EC0:0000256IHAMAPRule: MF 00812, EC0:0000256ISAAS:SAAS0089691 0}; EC=2.1.1.67 {EC0:00002561HAMAP-00812, EC0:0000256I SAAS:SAAS0089691 O}; AltName: Full=Thiopurine methyltransferase {ECO:00002561HAMAP—Rule:MF 00812};", Database accession No. A0A1L8MA47.
Database UniProt [Online] Jul. 24, 2013 (Jul. 24, 2013), "SubName: Full=Acyl-ACP thioesterase {EC0:00003131.EMBLCDD77481.1 };", retrieved from EBI accession No. UNIPROT:R7CHF5 Database accession No. R7CHF5.
Database UniProt [Online] Jun. 11, 2014, "RecName: Full= Thiopurine S-methyltransferase {EC0:0000256IHAMAPRule: MF 00812, EC0:0000256ISAAS:SAAS0089691O}; EC=2.1.1.67 {EC0:0000256IHAMAP—Rule:MF 00812, EC0:00002561 SAAS-:SAAS0089691 O}; AltName: Full=Thiopurine methyltransferase {ECO:0000256IHAMAP—Rule:MF 00812};", retrieved from EBI accession No. UNIPROT:AOA009ZVV4.

(56) References Cited

OTHER PUBLICATIONS

Devereaux, J., et al., "A comprehensive set of sequence analysis programs for the VAX", Nucleic Acids Research, vol. 12, Issue 1, Part 1, Jan. 11, 1984, pp. 387-395.
Final Office Action received for U.S. Appl. No. 16/372,092, dated Jul. 26, 2021, 10 Pages.
Final office action received for U.S. Appl. No. 16/398,351, dated Jul. 2, 2021, 24 pages.
Hensirisak et al. "Scale-Up of Microbubble Dispersion Generator for Aerobic Fermentation", Applied Biochemistry andBiotechnology vol. 101, 2002, p. 211-227 (Year: 2002).
https://www.clrblu.com/aeration/, "Aeration" (Year: 2021).
Hun-Suk, Song, et al., "Enhanced isobutanol production from acetate by combinatorial overexpression of acetyl-CoA synthetase and anaplerotic enzymes in engineered *Escherichia coli*", Biotechnology and Bioengineering, vol. 115, (May 2, 2018), XP002792879, pp. 1971-1978.
International Application Serial No. PCT/US2019/025194, Invitation to Pay Additional Fees dated Jul. 1, 2019, 14 pages.
International Application Serial No. PCT/US2019/025218, Invitation to Pay Additional Fees dated Jun. 25, 2019, 09 pages.
International Preliminary Report on Patentability for PCT application No. PCT/US2019/025211, dated Oct. 15, 2020, 13 pages.
Ishii et al., Uniprot database, accession No. G2J4X6, Nov. 2011.
Ishizuka, H., et al., "Putrescine Oxidase of Micrococcus Rubens: Primary Structure and *Escherichia coli*", Journal of General Microbiology, vol. 139, 1993, pp. 425-432.
Jones, G.W. and Kennedy, R.E., "Prevention of Gas Explosions by Controlling Oxygen Concentration", Industrial and Engineering Chemistry, vol. 27, Issue 11, 1935, pp. 1344-1346.
Judger, B-E., et al., "An analysis of the changes in soluble hydrogenase and global gene expression in Cupriavidusnecator (Ralstonia eutropha) H16 grown in heterotrophic diauxic batch culture", Microbial Cell Factories, vol. 14, 2015, pp. 1-11.
Kaster et al., "Increased Oxygen Transfer in a Yeast Fermentation Using a Microbubble Dispersion", Applied Biochemistry andBiotechnology vol. 24/25, 1990, p. 469-484 (Year: 1990).
Klasson, K.T., et al., "Bioreactor design for synthesis gas fermentations", Fuel, vol. 70, Issue 5, 1991, pp. 605-614.
Kyte, J., et al., "A simple method for displaying the hydropathic character of a protein", Journal of Molecular Biology, vol. 157, No. 1, May 5, 1982, pp. 105-132.
Lin, S., et al., "Biotin Synthesis Beings by Hijacking the Fatty Acid Synthesis Pathway," Nature Chemical Biology, vol. 6, No. 9, Sep. 2010, pp. 682-688.
Lucas et al., GenBank accession No. ACU95033, Aug. 26, 2009.
Maddipati, P., "Ethanol production from syngas by Clostridium strain P11 using corn steep liquor as a hutrientreplacement to yeast extract", Bioresoure Technology, vol. 102, Issue 11, 2011, pp. 6494-6501.
Manandhar, M., et al., "Pimelic acid, the first precursor of the Bacillus subtilis biotin synthesis pathway. exists as the free acid and is assembled by fatty acid synthesis: Bacillus subtilis biotin synthesis", Molecular Microbiology, vol. 104, No. 4, Mar. 3, 2017, pp. 595-607.
Meyers, et al., "Optimal alignments in linear space", Computer Applications in the Biosciences, vol. 4, 1988, pp. 11-17.
Needleman, S.B., et al., "A general method applicable to the search for similarities in the amino acid sequence of two proteins", Journal of Molecular Biology, vol. 48, Issue 3, Mar. 1970, pp. 443-453.
NETL brochure, "Syngas composition", accessed online on (www.netl.doe.gov/research/coal/energy systems/gasification/gasifipedia/syngas-composition), Jul. 3, 2021, total pp. 1-2. (Year: 2021).
Non Final Office Action received for U.S. Appl. No. 16/372,072, dated Mar. 6, 2020, 20 Pages.
Non Final Office Action received for U.S. Appl. No. 16/372,083, dated Apr. 27, 2021, 14 Pages.
Non Final Office Action received for U.S. Appl. No. 16/372,092, dated Mar. 4, 2021, 9 Pages.
Non Final Office Action received for U.S. Appl. No. 16/372,099, dated Jul. 9, 2021, 14 Pages.
Non-final office action received for U.S. Appl. No. 16/399,145, dated Aug. 12, 2020, 16 pages.
Pearson, W.R., et al., "Improved tools for biological sequence comparison", Proceedings of the National Academy of Science of the United States of America, vol. 85, Issue 8, Apr. 1988, pp. 2444-2448.
Phillips, J.R., et al., "Syngas Fermentation: A Microbial Conversion Process of Gaseous Substrates to Various Products", Fermentation, vol. 3, Issue 2, 2017, pp. 26.
Sadowski et al. "The sequence-structure relationship and protein function prediction", Current Opinion in Structural Biology, 19 pp. 357-362, 2009.
Seffernick et al., "Melelamine Deaminase and Atrazine Chlorohydrolase: 98 Percent Identical but Functionally Different", Journal of Bacteriology, 183(8) , pp. 2405-2410, 2001.
Shizaki, A., et al., "Microbial production of poly-D-3-hydroxybutyrate from C02", Applied Microbiology and Biotechnology, vol. 57, Oct. 2001, pp. 6-12.
Shulman, A.I., et al. "Structural determinants of allosteric ligand activation in RXR heterodimers," Cell, vol. 116, Issue 3, Feb. 6, 2004, pp. 417-429.
Slabu et al., "Discovery, Engineering and Synthetic Application of Transaminase Biocatalysts," ACS Catalysis 7, 2017, pp. 8263-8284.
Smith, T.F., et al., "Comparison of biosequences", Advances in Applied Mathematics, vol. 2, Issue 4, Dec. 1981, pp. 482-489.
Tanaka, K. and Ishizaki, A., "Production of poly-d-3-hydroxybutyric acid from carbon dioxide by a two-stage culture method employing Alcaligenes eutrophus ATCC 17697T", Journal of Fermentation and Bioengineering, vol. 77, Issue 4, 1994, pp. 425-427.
Tang et al., "Identification of Dehalobacter reductive dehalogenases that catalyse dechlorination of chloroform, 1, 1,1-trichloroethane and 1,1-dichloroethane", Phil Trans Royal Society Publishing, 368:20120318, pp. 1-10, 2013.
TPA: aspartate aminotransferase family protein [Betaproteobacteria bacterium], GenBank: HEL32111.1, Mar. 2, 2020, 1 page.
U.S. Appl. No. 16/399,155, Non Final Office Action dated Jul. 15, 2019, 19 Pages.
U.S. Appl. No. 16/399,155, Response filed Oct. 15, 2019 to Non-Final Office Action dated Jul. 15, 2019, 12 pages.
Pohlmann A. et al. ,"Phosphoenolpyruvate carboxykinase Cupriavidus necator H16", Gen Bank Q0K5F4, Retrieved from Internet URL: https://www.ncbi.nlm.nih.gov/protein/123133475?sat=35&satkey=13483043, Nov. 28, 2006, 01 page.
Pohlmann A. et al. ,"Phosphoenolpyruvate carboxylase Cupriavidus necator H16", Gen Bank Q0K7M4, Retrieved from Internet URL: https://www.ncbi.nlm.nih.gov/protein/123133692?sat=35&satkey=13483220, Nov. 28, 2006, 01 page.
Pohlmann A. et al. "Pyruvate carboxylase Cupriavidus necator H16", Gen Bank Q0KC80, Retrieved from Internet URL: https://www.ncbi.nlm.nih.gov/protein/Q0KC80, Nov. 28, 2006, 02 pages.
Bramer, C.O. et al. "Putative lyase protein", Gen Bank Q2Z1A9, Retrieved from Internet URL: https://www.ncbi.nlm.nih.gov/protein/122559031?sat=35&satkey=13062155, Oct. 31, 2006, 01 page.
Inui M et al. "Metabolic Engineering of Corynebacterium glutamicum for Fuel Ethanol Production under Oxygen Deprivation Conditions", J. Mol. Microbial. Biotechnol. 8, 2004, pp. 243-254.
Non-Final Rejection received for U.S. Appl. No. 16/398,401, dated Nov. 9, 2021, 38 Pages.
Final office action received for U.S. Appl. No. 16/398,351, dated Feb. 28, 2022, 11 pages.
KEGG Enzyme 1.6.1.1. Retrieved Feb. 22, 2022 (Year: 2022) pp. 1-2.
KEGG Enzyme 1.6.1.2. Retrieved Feb. 22, 2022 (Year: 2022) pp. 1-2.
KEGG Enzyme 7.1.1.1. Retrieved Feb. 22, 2022 (Year: 2022) pp. 1-2.
Non-final office action received for U.S. Appl. No. 16/372,106, dated Apr. 5, 2022, 33 pages.
Office Action received for U.S. Appl. No. 16/398,351, dated Jul. 5, 2022, 12 Pages.

(56) References Cited

OTHER PUBLICATIONS

Office Action received for U.S. Appl. No. 16/398,401, dated Sep. 1, 2022, 32 pages.
Ogawa et al., "Role of Phosphoenolpyruvate in the NADP-Isocitrate Dehydrogenase and Isocitrate Lyase Reaction in *Escherichia coli*", Journal of Bacteriology, vol. 189, No. 3, Feb. 2007, pp. 1176-1178.
Ghosalkar et al., "Oxygen Uptake Rate Measurement by Modified Dynamic Method and Effect of Mass-Transfer Rates on Growth of Pichia Stipitis : Modeling and Experimental Data Comparison", Austin Journal of Biotechnology & Bioengineering, vol. 3, Issue 3, 2016, 6 pages.
Kirk et al., "Quantification of the oxygen uptake rate in a dissolved oxygen-controlled oscillating jet-driven microbioreactor", Journal of Chemical Technology& Biotechnology, vol. 91, 2016, pp. 823-831.
Non-Final Office Action received for U.S. Appl. No. 16/372,092, dated Sep. 15, 2022, 11 pages.
Final office action received for U.S. Appl. No. 16/398,401, dated Feb. 6, 2023, 25 pages.
GenBank A6VKV4 GenBank 2012 p. 1-4.
GenBank Q0K4C1, GenBank, 2006; p. 1.
GenBank Q0K790, GenBank, 2006; p. 1.
GenBank Q46WX6, GenBank, 2006; p. 1-2.
GenBank Q474V2, GenBank, 2006; p. 1-2.
Satoshi Yuzawa et al., "Synthetic biology of polyketide synthases" Journal of Industrial Microbiology & Biotechnology vol. 45, No. 7, 2018, pp. 621-633.
GenBank CAQ69169.1, pp. 1-2. (Year: 2015).
GenBank Q8XWW2.1, pp. 1-2. (Year: 2015).
Non-Final Rejection received for U.S. Appl. No. 16/398,401 dated Jun. 22, 2023, pp. 18.
Final office action received for U.S. Appl. No. 16/372,092, mailed on Dec. 7, 2023, 14 pages.
Advisory Action received for U.S. Appl. No. 16/372,092, mailed on Oct. 7, 2021, 3 pages.
Advisory Action received for U.S. Appl. No. 16/372,099, mailed on Feb. 22, 2022, 3 pages.
Advisory Action received for U.S. Appl. No. 16/372,106, mailed on Mar. 9, 2022, 3 pages.
U.S. Appl. No. 16/372,083, Notice of Allowability mailed Sep. 22, 2021, 5 pages.
U.S. Appl. No. 16/372,083, Notice of Allowance mailed Aug. 31, 2021, 9 pages.
U.S. Appl. No. 16/372,083, Response filed Jul. 27, 2021 to Non-Final Office Action mailed Apr. 27, 2021, 11 pages.
U.S. Appl. No. 16/372,083, Supplemental Amendment filed for Non-Final Office Action mailed Apr. 27, 2021, 8 pages.
U.S. Appl. No. 16/372,092, Response filed Sep. 21, 2021 to Final Office Action mailed Jul. 26, 2021, 11 pages.
U.S. Appl. No. 16/372,106, Non-Final Office Action mailed Apr. 30, 2021, 26 pages.
U.S. Appl. No. 16/372,106, Response filed Jan. 19, 21 to Restriction Requirement mailed Dec. 28, 2020, 8 pages.
U.S. Appl. No. 16/372,106, Response filed Jun. 15, 2021 to Non-Final Office Action mailed Apr. 30, 2021, 12 pages.
U.S. Appl. No. 16/372,106, Restriction Requirement mailed Dec. 28, 2020, 7 pages.
Baltz et al. "Manual of Industrial Microbiology and Biotechnology", ASM Press, 2010, 4 Pages (Abstract).
Berg et al." Biochemistry 5th ed.", W H Freeman and Company, 2002, 1 Page (Abstract).
Final Rejection received for U.S. Appl. No. 16/372,099, mailed on Dec. 21, 2021, 17 pages.
Final Rejection received for U.S. Appl. No. 16/372,106, mailed on Dec. 22, 2021, 32 pages.
Final Rejection received for U.S. Appl. No. 16/372,106, mailed on Oct. 4, 2021, 29 pages.
Folsom et al., "Physiological and Proteomic Analysis of *Escherichia coli* Iron-Limited Chemostat Growth," Journal of Bacteriology, vol. 196, No. 15, Aug. 2014, pp. 2748-2761.
Harder et al., "Physiological responses to nutrient limitation", Annual Review of Microbiology, vol. 37, 1983, pp. 1-23.
Huang et al., "Bacterial and Yeast Cultures—Process Characteristics, Products, and Applications", Bioprocessing for Value-Added Products from Renewable Resources, Dec. 2007, pp. 185-223.
International Application Serial No. PCT/US2019/025189, International Preliminary Report on Patentability mailed Oct. 15, 2020, 9 pages.
International Application Serial No. PCT/US2019/025194, International Preliminary Report on Patentability mailed Oct. 15, 20, 15 pages.
International Application Serial No. PCT/US2019/025202, International Preliminary Report on Patentability mailed Oct. 15, 20, 12 pages.
International Application Serial No. PCT/US2019/029795, International Preliminary Report on Patentability mailed Nov. 12, 20, 8 pages.
International Application Serial No. PCT/US2019/029798, International Preliminary Report on Patentability mailed Nov. 12, 20, 14 pages.
International Application Serial No. PCT/US2019/029817, International Preliminary Report on Patentability mailed Nov. 12, 20, 14 pages.
International Application Serial No. PCT/US2019/029827, International Preliminary Report on Patentability mailed Nov. 12, 20, 14 pages.
International Application Serial No. PCT/US2019/029956, International Preliminary Report on Patentability mailed Nov. 12, 20, 12 pages.
International Application Serial No. PCT/US2019/029973, International Preliminary Report on Patentability mailed Nov. 12, 20, 12 pages.
Kihlberg,"The Microbe as a Source of Food" Annual Review of Microbiology, vol. 26, 1972, 427-466.
Maqbool, A. et al., "Multispecies: CmpA/NrtA family ABC transporter substrate-binding protein [Cupriavidus]", Retrieved from internet https://www.ncbi.nlm.nih.gov/protein/WP_010814804.1/, Mar. 20, 2023, 2 pages.
Non-Final Rejection received for U.S. Appl. No. 16/372,092, mailed on Sep. 15, 2022, 11 pages.
Notice of Allowance received for U.S. Appl. No. 16/372,099, mailed on Apr. 15, 2022, 11 pages.
Response to Final Office Action for U.S. Appl. No. 16/372,099, filed Feb. 8, 2022, 9 pages.
Response to Final Rejection for U.S. Appl. No. 16/372,106, filed Dec. 9, 2021, 9 pages.
Response to Final Rejection for U.S. Appl. No. 16/372,106, filed on Feb. 16, 2022, 9 pages.
Response to Non-Final Office Action for U.S. Appl. No. 16/372,099, filed Oct. 7, 2021, 8 pages.
Response to Non-Final Rejection for U.S. Appl. No. 16/372,092, filed Feb. 28, 2022, 9 pages.
Stanbury et al. "Principles of Fermentation Technology", 3rd Edition, Aug. 31, 2016, 4 Pages.(Abstract).
Yonezuka, K. et al., "Phosphonate C-P lyase system protein PhnG [Cupriavidus necator]", Retrived from internet https://www.ncbi.nlm.nih.gov/protein/KUE89182.1, Dec. 23, 2015, 2 pages.
Non-Final Rejection received for U.S. Appl. No. 16/372,092, mailed on Nov. 26, 2021, 10 Pages.
Final office action received for U.S. Appl. No. 16/372,092, mailed on Mar. 28, 2024, 12 pages.
Lopes et al., "Over-Pressurized Bioreactors: Application to Microbial Cell Cultures", American Institute of Chemical Engineers, vol. 30, No. 4, 2014, pp. 767-774.

* cited by examiner

MATERIALS AND METHODS FOR CONTROLLING LIMITATION CONDITIONS IN PRODUCT BIOSYNTHESIS FOR NON-PHB GENERATING SPECIES OF THE GENERA *RALSTONIA* OR *CUPRIAVIDUS* AND ORGANISMS RELATED THERETO

PRIORITY CLAIM

The present application claims the benefit of U.S. Provisional Patent Application No. 62/665,751 filed May 2, 2018, which is incorporated by reference herein for all purposes.

SEQUENCE LISTING

The instant application contains a Sequence Listing which has been filed electronically in ASCII format and is hereby incorporated by reference in its entirety. Said ASCII copy, created on Jul. 26, 2019, is named 061646-1135300_(01001US)_SL.txt and is 1,430 bytes in size.

FIELD

The present disclosure relates generally to increasing non-biomass and non-polyhydroxyalkanoate product yield in an organism. In particular, the present disclosure relates to the aerobic continuous culturing of the organism under one or more specific limitation conditions and/or stress response conditions, and to the modification of the organism with one or more promoters which are constitutive or inducible under one or more specific limitation conditions.

BACKGROUND

Organisms have a limited ability to control their environment and therefore may respond to environmental conditions by changing themselves. Such changes have been reported to include genotypic changes, wherein the microorganism may express certain sets of genes to be functionally and structurally adjusted to a set of conditions, or phenotypic responses of a given genotype to environmental changes, which confers a high level of versatility. In industrial bioprocesses, growth can be manipulated by limiting the availability of certain nutrients, or by depriving specific nutrients altogether, to force a productive microbial physiological state (Harder, W., & Dijkhuizen, L. Annual Review of Microbiology 1983 37(1):1-23). This is because under conditions of nutrient limitation a phenomenon known as overflow metabolism (also known as energy spilling uncoupling or spillage) occurs in many bacteria (Russell, J. B. Journal of Molecular Microbiology and Biotechnology 2007 13:1-11). In growth conditions in which there is a relative excess of a carbon source but other nutrients (e.g. phosphorous, nitrogen and/or oxygen) are limiting cell growth, overflow metabolism results in the utilization of such excess energy (or carbon), not for biomass formation but for the excretion of metabolites, typically organic acids.

In *Cupriavidus necator* (*C. necator*), a modified form of overflow metabolism occurs, in which excess carbon is sunk into the intracellular storage carbohydrate polyhydroxybutyrate (PHB). PHB is a key intracellular carbon and energy storage compound enabling the cells to survive periods of starvation and other stressful conditions. When utilizing *Cupriavidus* or *Ralstonia* for the purposes of generating other chemical products, however, this increased polyhydroxyalkanoate production is detrimental for obtaining high productivities and/or yields of the alternate products. As a result, elimination or significant attenuation of polyhydroxyalkanoate synthesis can be required to maximize the efficiency of generating the other more desired products. Using this strategy, strains of *C. necator* which are deficient in PHB synthesis have been observed to instead produce different extracellular overflow metabolites. The range of metabolites that have been detected in PHB deficient *C. necator* strains include acetate, acetone, butanoate, cis-aconitate, citrate, ethanol, fumarate, 3-hydroxybutanoate, propan-2-ol, malate, methanol, 2-methyl-propanoate, 2-methyl-butanoate, 3-methyl-butanoate, 2-oxoglutarate, meso-2,3-butanediol, acetoin, DL-2,3-butanediol, 2-methyl-propan-1-ol, propan-1-ol, lactate 2-oxo-3-methylbutanoate, 2-oxo-3-methylpentanoate, propanoate, succinate, formic acid, and pyruvate. The type and productivity of overflow metabolites generated in a particular fermentation can depend upon the type of limitation applied (e.g. nitrogen, phosphate, oxygen), the extent of the limitation, and the carbon source provided (Vollbrecht et al. European J. Appl. Microbiol. Biotechnol. 1978 6:145-155; Vollbrecht et al. European J. Appl. Microbiol. Biotechnol. 1978 6:157-166; Vollbrecht et el. European J. Appl. Microbiol. Biotechnol 1979 7:267-276).

For the commercial synthesis of PHB in *C. necator*, batch or fed-batch fermentation cultures are typically operated under unbalanced growth conditions in which a carbon source is present in excess and another microelement is simultaneously depleted simultaneously. Nitrogen limitation is typically employed as this is reported to induce the greatest PHB response. Limitation of phosphate has also been utilized successfully (Harder, W., & Dijkhuizen, L. Annual Review of Microbiology 1983 37(1):1-23; Wang and Lee Applied and Environmental Microbiology 1997 63(9):3703-3706). Similar limitation strategies and fermentation configurations have been implemented in *Cupriavidus* strains engineered for other biochemical production. For example, the utilization of nitrogen or phosphate limitation has been used in generation of ethanol, isopropanol, branched-chain alcohols, and 2-hydroxyisobutyrate (Grosseau et al Appl. Microbiol. Biotechnol. 2014 98(9):4277-90; Lee et al. Biotechnology and Bioprocess Engineering 2016 21(3):402-407; Pryzbylski et al. Appl. Microbiol. Technol. 2013 97(20):8875-85; Lu et al. Appl. Microbiol. Technol. 2012 96(1): 283-97). However, these limitation strategies and culture conditions can have disadvantages associated with the generation of nitrogenous products with nitrogen limitation, an altered physicochemical composition of the cell membrane under phosphate limitation, and productivity and efficiency limitations associated with batch or fed-batch processes.

Despite these disadvantages, significant motivations remain to further develop bioprocesses for the production of a variety of chemicals, including but not limited to naturally occurring overflow metabolites in *Cupriavidus* or *Ralstonia*. The replacement of traditional chemical production processes that rely on, for example, fossil fuels and/or potentially toxic chemicals, with more sustainable and environmentally friendly continues to be considered. This "green chemistry" or "cleantech" research and development includes work to identify biological routes to suitable building blocks for such use in the manufacturing of a variety of chemicals. Accordingly, there exists a need for identifying and applying suitable nutrient limitation approaches in preferably continuous fermentation conditions for improved extracellular product formation. The following disclosure addresses this and other needs.

SUMMARY

The present disclosure generally relates to methods for synthesizing an extracellular product with an organism cultured in a continuous fermentation system, wherein the yield and productivity of the product are increased as a result of particular modifications to the organism, and operational conditions of the fermentation system.

In one aspect, the disclosure is to a method for increasing the yield of an extracellular product in an aerobic fermentation system. The method includes providing an organism belonging to a genus selected from the group consisting of *Cupriavidus* and *Ralstonia*. The organism has been modified to exhibit a decreased synthesis of polyhydroxyalkanoate relative to that of the corresponding wild type organism. The organism has been further modified to exhibit an increased or newly introduced synthesis of the extracellular product relative to that of the corresponding wild type organism. The organism includes one or more modified or exogenous promoters. The promoters are each independently a constitutive promoter or an inducible promoter activated by a nutrient limitation condition. The method further includes culturing a population of the organism in the fermentation system. The method further includes independently controlling the concentration of each of one or more selected limiting nutrients in at least one reactor of the fermentation system, wherein each limiting nutrient independently has a limiting concentration. The method further includes operating the fermentation system under continuous fermentation conditions suitable for synthesis of the extracellular product by the organism. The continuous fermentation conditions include concentrations of the selected limiting nutrients less than their respective limiting concentrations in the at least one reactor. The yield of the extracellular product is increased relative to that synthesized by the organism under otherwise corresponding continuous fermentation conditions that include concentrations of at least one of the selected limiting nutrients above its limiting concentration in each reactor of the fermentation system.

In another aspect the disclosure relates to a non-naturally occurring organism belonging to a genus selected from the group consisting of *Cupriavidus* and *Ralstonia*. The organism has been modified to exhibit a decreased synthesis of polyhydroxybutyrate relative to that of the corresponding wild type organism. The organism has been further modified to exhibit an increased or newly introduced synthesis of an extracellular product relative to that of the corresponding wild type organism. The organism includes one or more modified or exogenous promoters. The promoters are each independently an inducible promoter activated by a nutrient limitation condition. Synthesis of the extracellular product by the organism is increased when the inducible promoters are activated.

In another aspect, the disclosure is to an extracellular product. The extracellular product is made using the method disclosed herein.

BRIEF DESCRIPTION OF DRAWINGS

The disclosure references the appended drawings, wherein like numerals designate similar parts.

DETAILED DESCRIPTION

Figure 1:
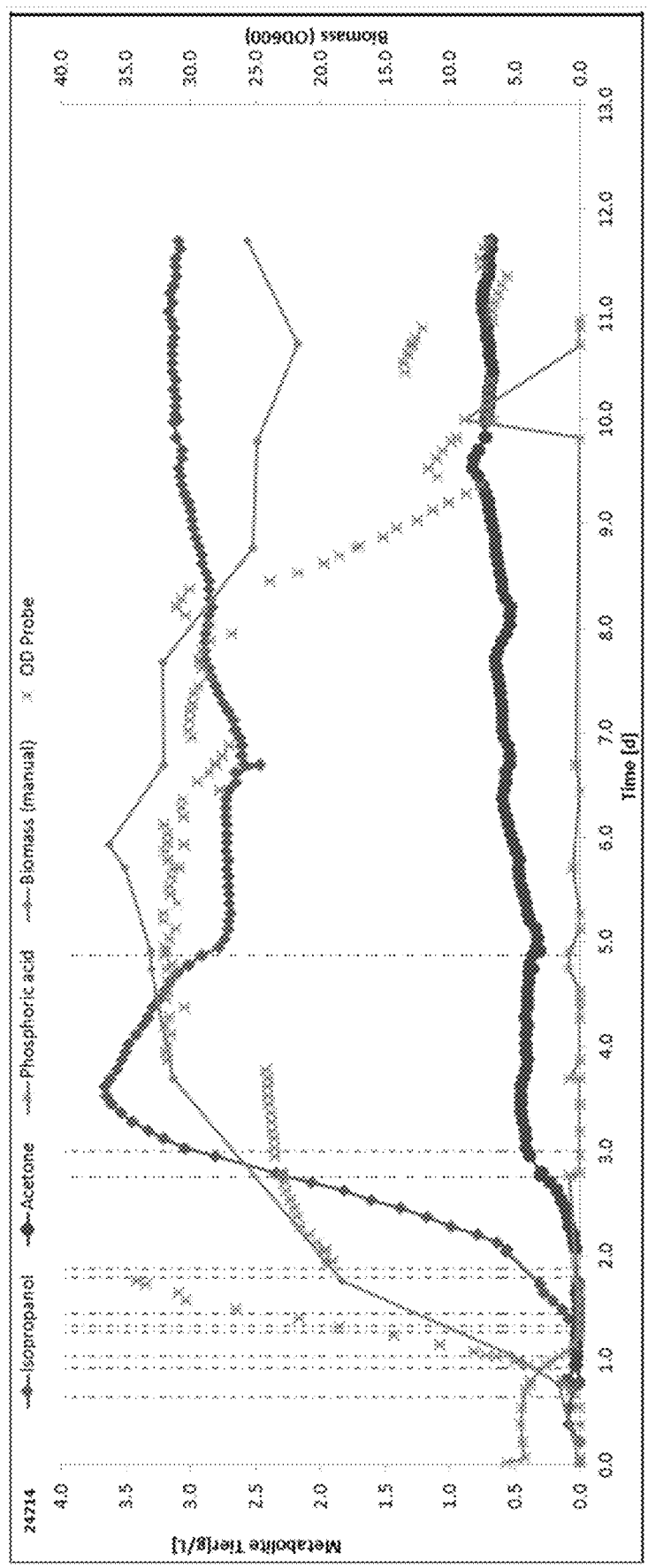
FIG. 1 is a graph showing reactor conditions for isopropanol production by an organism having a phosphorous-limitation inducible promoter and cultured under limited phosphate in a loop reactor.

The present disclosure provides materials, methods, and strategies related to particular nutrient limitation conditions for organisms, thereby improving carbon uptake and conversion to desired extracellular chemical products. The present disclosure also provides for the use of specific promoters that respond under particular limitation conditions. Product pathway enzymes may confer a heavy metabolic burden upon the cell, impairing cell growth and reducing viability. To maximize product yields, it can be advantageous to limit the expression of genes associated with the product pathway to a production phase. This can be achieved using promoters that govern high-level gene expression under conditions of nutrient-limitation to control the expression of genes at the transcriptional level. Accordingly, the present invention provides methods for increasing product yield in an organism.

In one non-limiting embodiment, the method includes providing an organism belonging to a genus selected from the group consisting of *Cupriavidus* and *Ralstonia*, or an organism with similar properties thereto. In certain aspects, the organism is a *Cupriavidus necator, Cupriavidus metallidurans, Cupriavidus taiwanensis, Cupriavidus pinatubonensis, Cupriavidus basilensis*, or *Ralstonia pickettii*, or an organism with similar properties thereto. In some embodiments, the organism is *Cupriavidus necator* or an organism with properties similar thereto.

*Cupriavidus necator* (also referred to as *Hydrogenomonas eutrophus, Alcaligenes eutropha, Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *Cupriavidus necator* include microaerophilicity, copper resistance (Makar and Casida; 1987), bacterial predation (Byrd et al., 1985; Sillman & Casida, 1986; Zeph & Casida, 1986) and polyhydroxybutyrate (PHB) synthesis. In addition, the cells have been reported to be capable of both aerobic and nitrate dependent anaerobic growth. A non-limiting example of a *Cupriavidus necator* organism useful in the present invention is a *Cupriavidus necator* of the H16 strain. In one non-limiting embodiment, a *Cupriavidus necator* host of the H16 strain with at least a portion of the phaCAB gene locus knocked out is used. Reference to an organism with properties similar to those of the groups and species disclosed herein indicates that the organism has one or more of the aforementioned properties of *Cupriavidus necator*.

In some embodiments, the provided organism has been modified to have one or more different characteristic properties relative to those of the corresponding unmodified wild type organism. For example, the organism can be modified to have decreased or eliminated intracellular polyhydroxyalkanoate synthesis and increased or newly introduced extracellular product synthesis. In certain aspects, the organism is modified by altering, engineering, or introducing one or more nucleic acid sequences within the organism. The altering of modifying of the nucleic acid sequences can be, for example and without limitation, via genetic engineering, by adaptive mutation, or by selective isolation of naturally occurring mutant strains.

In some embodiments, one or more enzymes or nucleic acids of the organism are modified via non-direct or rational enzyme design approaches with aims of introducing one or more new synthetic pathways, improving activity, improving specificity, reducing feedback inhibition, reducing repression, improving enzyme solubility, changing stereospecificity, or changing co-factor specificity. In some embodiments, the enzymes in the pathways outlined herein can be gene dosed (i.e., overexpressed by having a plurality of copies of the gene in the host organism), into the resulting genetically modified organism via episomal or chromosomal integration approaches. In some embodiments, genome-scale system biology techniques such as Flux Balance Analysis can be utilized to devise genome scale attenuation or knockout strategies for directing carbon flux. Attenuation strategies include, but are not limited to, the use of transposons, homologous recombination (double cross-over approach), mutagenesis, enzyme inhibitors, and RNA interference (RNAi). In some embodiments, fluxomic, metabolomic and transcriptomal data can be utilized to inform or support genome-scale system biology techniques, thereby devising genome-scale attenuation or knockout strategies in directing carbon flux. In some embodiments, the tolerance of the host microorganism to high concentrations of the extracellular product can be improved through continuous cultivation in a selective environment.

The modified nucleic acid sequences of the organism can include, for example, one or more enzymes, one or more promoters, one or more transcription factors, or combinations thereof. The modifications can be to nucleic acids directly involved in synthetic pathways leading to polyhydroxyalkanoate and/or the extracellular product. The modifications can be to nucleic acids not directly involved in these synthetic pathways, but indirectly affecting the pathways through the interconnected metabolic network and metabolic control strategy of the organism. The modification of the nucleic acid sequences can include one or more deletions, one or more substitutions, one or more insertions, or combinations thereof.

Enzymes with substitutions will generally have not more than 50 (e.g., not more than 1, not more than 2, not more than 3, not more than 4, not more than 5, not more than 6, not more than 7, not more than 8, not more than 9, not more than 10, not more than 12, not more than 15, not more than 20, not more than 25, not more than 30, not more than 35, not more than 40, or not more than 50) amino acid substitutions (e.g., conservative or non-conservative substitutions). This applies to any of the enzymes described herein and functional fragments thereof. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic, or acidic groups by another member of the same group can be deemed a conservative substitution. In contrast, a non-conservative substitution is a substitution of one amino acid for another with dissimilar characteristics.

Deletion variants can, for example, lack 1, 2, 3, 4, 5, 6, 7, 8, 9, 10, 11, 12, 13, 14, 15, 16, 17, 18, 19, or 20 amino acid segments (of two or more amino acids) or non-contiguous single amino acids.

In one non-limiting embodiment, modification of the organism is carried out by allele exchange. In this embodiment, genome edits are made in an organism such as *C. necator* by allele exchange (also referred to as allelic exchange). In one non-limiting embodiment, a *Cupriavidus necator* host of the H16 strain with at least a portion of the phaCAB gene locus knocked out is used. In one non-limiting embodiment, the organism is a ΔphaCAB H16 *C. necator* strain generated using allele exchange.

The term 'allele' is often used interchangeably with the term 'gene' more generally and refers to a defined genomic locus. In allele exchange, a specific run of DNA sequence (i.e., the native allele) in a genome of an organism is literally exchanged for a recombinant, mutant, or synthetic run of DNA sequence (i.e., the recombinant allele). Depending on the nature of the recombinant allele, this allele exchange can result in a gene deletion, a gene substitution, or a gene insertion.

In one non-limiting embodiment, recombinant/synthetic alleles can be constructed via gene synthesis and/or standard molecular biology techniques. These alleles are then cloned into a plasmid vector for transfer into the organism and execution of the allele exchange procedure.

In some embodiments, the organism is modified to include one or more exogenous nucleic acid sequences. The term "exogenous" as used herein with reference to a nucleic acid (or a protein) refers to a nucleic acid that does not occur in (and cannot be obtained from) a cell or organism of that particular type as it is found in nature, or to a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is a non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by a polymerase chain reaction (PCR) or restriction endonuclease treatment, as well as cDNAs, are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of organism x is an exogenous nucleic acid with respect to a cell of organism y once that chromosome is introduced into a cell of organism y.

In certain aspects, the organism is modified to include one or more functional fragments of enzymes, other polypeptides, or nucleic acids. The phrase "functional fragment" as used herein refers to a peptide fragment of a polypeptide or a nucleic acid sequence fragment encoding a peptide fragment of a polypeptide that has at least 25%, e.g., at least 30%, at least 40%, at least 50%, at least 60%, at least 70%, at least 75%, at least 80%, at least 85%, at least 90%, at least 95%, at least 98%, at least 99%, or at least 100% of the activity of the corresponding mature, full-length, polypeptide. The functional fragment can generally, but not always, be comprised of a continuous region of the polypeptide, wherein the region has functional activity.

In some embodiments, the organism of the provided method has been modified to exhibit a decreased or diminished synthesis of polyhydroxyalkanoate relative to that of the corresponding wild type organism. Organisms used in this disclosure can exhibit at least 20%, e.g., at least 25%, at least 30%, at least 40%, or at least 50%, decreased polyhydroxyalkanoate synthesis as compared to the corresponding unperturbed wild-type organism of the same species. In certain aspects, the polyhydroxyalkanoate is not synthesized by the modified organism. In some embodiments, the polyhydroxyalkanoate is polyhydroxybutyrate, polyhydroxyvalerate, or a combination thereof.

In some embodiments, the organism of the provided method has been modified to exhibit an increased synthesis of the extracellular product relative to that of the corresponding wild type organism. The extracellular product synthesis by the organism can be increased by, for example, more than 5%, e.g., more than 8%, more than 13%, more than 20%, more than 32%, more than 50%, more than 79%, more than 130%, more than 200%, more than 320%, or more than 500% relative to that of the corresponding wild type organism. In certain aspects, the wild type organism does not synthesize the extracellular product.

The organism can be modified to, for example, express one or more of a malonyl-[acp] O-methyltransferase, a pimeloyl-[acp] methyl ester methylesterase, a β-ketothiolase, a β-ketoacyl-[acp] synthase, a β-ketothiolase, a 3-oxoacyl-[acp] reductase, acetoacetyl-CoA reductase, a 3-hydroxyacyl-CoA dehydrogenase, a 3-hydroxybutyryl-CoA dehydrogenase, an enoyl-CoA hydratase, 3-hydroxyacyl-[acp] dehydratase, an enoyl-[acp] reductase, a trans-2-enoyl-CoA reductase, a thioesterase, a reversible CoA ligase, a CoA-transferase, an acetylating aldehyde dehydrogenase, a 5-oxopentanoate dehydrogenase, a 6-oxo-cyclohex-1-ene-carbonyl-CoA hydrolase, an enoyl-CoA hydratase, a 6-oxohexanoate dehydrogenase, a 7-oxoheptanoate dehydrogenase, an aldehyde dehydrogenase, a carboxylate reductase, an ω-transaminase, an N-acetyl transferase, an alcohol dehydrogenase, a deacetylase, a 6-hydroxyhexanoate dehydrogenase, a 2-ketocyclohexanecarboxyl-CoA hydrolase, a glutaconyl-CoA decarboxylase, a glutaryl-CoA dehydrogenase, a 3-hydroxyacyl-CoA dehydrogenase, a 6-hydroxycyclohex-1-ene-1-carboxyl-CoA dehydrogenase, a cyclohexa-1,5-dienecarbonyl-CoA hydratase, a cyclohex-1-ene-1-carboxyl-CoA dehydrogenase, a cyclohex-1-ene-1-carboxyl-CoA hydratase, a 2-hydroxycyclohexanecarboxyl-CoA dehydrogenase, a thioesterase, a 4-hydroxybutyrate dehydrogenase, a 5-hydroxypentanoate dehydrogenase, a deacetylase, and a lysine N-acetyl transferase.

The organism can be modified to, for example, attenuate or eliminate the activity of one or more of polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating an NADH or NADPH imbalance, a glutamate dehydrogenase dissipating an NADH or NADPH imbalance, an NADH/NADPH-utilizing glutamate dehydrogenase, a pimeloyl-CoA dehydrogenase, an acyl-CoA dehydrogenase accepting C7 building blocks and central precursors as substrates, a glutaryl-CoA dehydrogenase, and a pimeloyl-CoA synthetase.

The organism can be modified to, for example, overexpress or introduce the activity of one or more of an acetyl-CoA synthetase, a 6-phosphogluconate dehydrogenase, a transketolase, a pyridine nucleotide transhydrogenase, a formate dehydrogenase, a glyceraldehyde-3P-dehydrogenase, a malic enzyme, a glucose-6-phosphate dehydrogenase, a fructose 1,6 diphosphatase, an L-alanine dehydrogenase, an L-glutamate dehydrogenase specific to an NADH or NADPH used to generate co-factor imbalance; a methanol dehydrogenase, a formaldehyde dehydrogenase, a diamine transporter; a dicarboxylate transporter, an S-adenosylmethionine synthetase, and a multidrug transporter.

In some embodiments, the organism is modified to increase the efflux or secretion of the extracellular product. Such modifications can include, for example, those that alter the structure of the cell membrane of the organism, or that increase or introduce active or passive transporter activity related to export of the extracellular product.

The extracellular product can be, for example and without limitation, a $C_{3-12}$ organic acid, an alcohol, an olefin, a $C_{6-12}$ hydroxyacid, a fatty acid, an amino acid, an alkane, an alkene, an isoprenoid, a $C_{6-12}$ amino acid, a $C_{6-12}$ diamine, a $C_{6-12}$ difunctional aliphatic fatty acid or a derivative thereof, a $C_{6-12}$ diol, a $C_{6-12}$ diacid, or a combination thereof. The extracellular product can include, for example, methionine, threonine, lysine, glutamic acid, tryptophan, aspartic acid, citric acid, maleic acid, succinic acid, isoprene, linalool, limonene, 3-hydroxypropanoic acid, 1,2-propanediol, 1,3-propanediol, malonic acid, lactic acid, n-butanol, 2-butanone, butadiene, 2,3-butanediol, 1,3-butanediol, benzoic acid, 1,4-benzenediamine, benzeneamine, pentamethylene diamine, pyrimidine, vanillin, hydroquinone, 1,4-diaminobutane, 2-hydroxyisobutyric acid, itaconic acid, 3-hydroxybutyrate, one or more nylon intermediates, or a combination thereof.

In some embodiments, the extracellular product includes acetate, acetone, butanoate, citrate, ethanol, fumarate, 3-hydroxybutanoate, propan-2-ol, malate, methanol, meso-2,3-butanediol, acetoin, DL-2,3-butanediol, propan-1-ol, lactate, propanoate, succinate, formic acid, or a combination thereof.

In some embodiments, the extracellular product includes pimelic acid, 7-aminoheptanoate, 7-hydroxyheptanoate, heptamethylenediamine, 1,7-heptanediol, or a combination thereof. Additional descriptions of the synthesis of these extracellular products with *Ralstonia, Cupriavidus*, or an organism related thereto can be found in U.S. Pat. No. 10,196,657, the disclosure of which is incorporated by reference herein in its entirety for all purposes.

In some embodiments, the extracellular product includes 1,4-butanediol, putrescine, 4-hydroxybutyrate, 4-aminobutyrate, or a combination thereof. Additional descriptions of the synthesis of these extracellular products with *Ralstonia, Cupriavidus*, or an organism related thereto can be found in U.S. Pat. Nos. 10,072,150 and 9,637,764, the disclosures of which are incorporated by reference herein in their entirety for all purposes.

In some embodiments, the extracellular product includes glutaric acid, 5-aminopentanoic acid, cadaverine (also known as 1,5 pentanediamine), 5-hydroxypentanoic acid, 1,5-pentanediol, glutarate semialdehyde (also known as 5-oxopentanoate), or a combination thereof. Additional descriptions of the synthesis of these extracellular products with *Ralstonia, Cupriavidus*, or an organism related thereto can be found in U.S. Pat. No. 9,920,339, the disclosure of which is incorporated by reference herein in its entirety for all purposes.

In some embodiments, the extracellular product includes isoprene. Additional descriptions of the synthesis of this extracellular product with *Ralstonia, Cupriavidus*, or an organism related thereto can be found in U.S. Pat. No. 9,862,973, the disclosure of which is incorporated by reference herein in its entirety for all purposes.

In some embodiments, the extracellular product includes adipic acid, 6-aminohexanoic acid, hexamethylenediamine, caprolactam, 1,6-hexanediol, or a combination thereof. Additional descriptions of the synthesis of these extracellular products with *Ralstonia, Cupriavidus*, or an organism related thereto can be found in U.S. Pat. No. 9,580,733, the disclosure of which is incorporated by reference herein in its entirety for all purposes.

For extracellular products containing carboxylic acid groups such as organic monoacids, hydroxyacids, aminoacids and dicarboxylic acids, these products can be formed or converted to their ionic salt form when an acidic proton present in the parent product either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate and/or bicarbonate, sodium hydroxide, ammonia, and the like. The salt can be isolated as is from the system as a salt or converted to the free acid by reducing the pH to below the lowest pKa through addition of acid or treatment with an acidic ion exchange resin.

For extracellular products of the present invention containing amine groups, such as but not limited to organic amines, amino acids and diamine, these products can be formed or converted to their ionic salt form by addition of an acidic proton to the amine to form the ammonium salt; formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, or muconic acid. The salt can be isolated as is from the system as a salt or converted to the free amine by raising the pH to above the lowest pKa through addition of base or treatment with a basic ion exchange resin. Acceptable inorganic bases are known in the art and include aluminum hydroxide, calcium hydroxide, potassium hydroxide, sodium carbonate and/or bicarbonate, ammonia, sodium hydroxide, and the like.

For extracellular products containing both amine groups and carboxylic acid groups, such as but not limited to amino acids, these products can be formed or converted to their ionic salt form by acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases include aluminum hydroxide, calcium hydroxide, potassium hydroxide, sodium carbonate, sodium hydroxide, and the like. The products can also be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate and/or bicarbonate, ammonia, sodium hydroxide, and the like. The salt can be isolated as is from the system or converted to the free acid by reducing the pH to below the lowest pKa through addition of acid or treatment with an acidic ion exchange resin.

In some embodiments, the organism includes one or more modified or exogenous promoters. In certain aspects, the organism includes one or more modified promoters. In certain aspects, the organism includes one or more exogenous promoters. In certain aspects, the organism includes one or more modified promoters, and one or more exogenous promoters. Within an engineered pathway, the modified enzymes and/or promoters can be from a single source, i.e., from one species or genus, or can be from multiple sources, i.e., different species or genera.

In some embodiments, each of the modified or exogenous promoters are independently either a constitutive promoter or an inducible promoter that are activated by a nutrient limitation condition. In certain aspects, at least one of the modified or exogenous promoters is a constitutive promoter. In certain aspects, each of the modified or exogenous promoters is independently a constitutive promoter. In certain aspects, at least one of the modified or exogenous promoters is an inducible promoter activated by nutrient limitation conditions. In certain aspects, each of the modified or exogenous promoters is independently an inducible promoter activated by a nutrient limitation condition.

Non-limiting examples of specific limitation conditions under which the organisms of the present invention can be cultured include iron limitations, sulphate limitations, nitrogen limitations, potassium limitations, oxygen limitations, phosphorus limitations, carbon limitations, and gradients and combinations thereof. For example, specific iron and/or sulphate limitation can impact the synthesis of iron-sulphur proteins and cytochromes and can manipulate the electron transport chains of the organism. This specific limitation condition can be used alone or in combination with nitrogen and/or phosphorus limitation to increase the production of organic acids including, but not limited to, lactic acid, acetic acid, formic acid, and pyruvic acid. The specific limitation condition of a potassium gradient can be used to generate products of oxidative metabolism. This specific limitation condition can be used alone or in combination with nitrogen and/or phosphorus limitation to increase the synthesis of organic acids including, but not limited to, lactic acid, acetic acid, formic acid and pyruvic acid. The specific limitation condition of oxygen limitation can be utilized to disrupt the redox balance of the organism. Oxygen limitation can be used alone or in combination with nitrogen and/or phosphorus limitation, iron and/or sulphur limitation, and/or potassium limitation to increase the synthesis of organic acids including, but not limited to, lactic acid, acetic acid, formic acid and pyruvic acid. In some embodiments, the nutrient limitation conditions include a nitrogen limitation condition, a phosphorous limitation condition, and an oxygen limitation condition.

In addition, the specific limitation condition of carbon limitation with concurrent carbon feedstock utilization can be used to achieve increased carbon uptake in the organism. In one non-limiting embodiment, a carbon source is continually supplied at a rate equal to, or within, 5% of product formation for carbon limitation. Carbon limitation can be used alone or in combination with oxygen and/or nitrogen and/or phosphorus and/or iron and/or sulphur and/or potassium limitation.

Stress conditions can also be used to activate inducible promoters responsive to these conditions. Non-limiting examples of stress response conditions include physical environmental conditions that can be imposed on the organism such as temperature and pressure.

In some embodiments, the method further includes culturing a population of the provided organism in a fermentation system. The cultured population can be a substantially pure culture of the provided organism. As used herein, the phrase "substantially pure culture" refers to a culture or population of the organism in which less than 20%, e.g., less than 15%, less than 10%, less than 5%, less than 2%, less than 1%, less than 0.5%, less than 0.25%, less than 0.1%, less than 0.01%, less than 0.001%, or less than 0.0001% of the total number of viable cells in the culture are viable cells other than the altered microorganism, e.g., other bacterial, fungal (including yeast), mycoplasmal, or protozoan cells. The culture of the organism population includes the cells and a growth, storage, or transport medium. Media can be liquid, semi-solid (e.g., gelatinous media), or frozen.

Non-limiting examples of fermentation systems suitable for use with the methods disclosed herein include a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced circulation, a bubble column fermenter, a fixed (packed)-bed column fermenter, a single horizontal fermenter having multiple compartments, and a multistage column fermenter. Each individual fermenter or autoclave of the fermentation system can also be referred to herein as a reactor or bioreactor of the fermentation system.

In some embodiments, the method further includes independently controlling the concentration of each of one or more selected limiting nutrients in at least one reactor of the fermentation system. The number of limiting nutrients having their concentrations controlled can be, for example, one, two, three, four, five, six, seven, eight, nine, ten, or more than ten. In certain aspects, the concentration of each of the one or more selected limiting nutrients is controlled in each reactor of the fermentation system.

Non-limiting examples of limiting nutrients for the organism and methods disclosed herein include nitrogen, phosphorous, iron, sulphate, potassium, and oxygen. In certain aspects, the one or more selected limiting nutrients include nitrogen. In certain aspects, the one or more limiting nutrients include phosphorous.

For embodiments in which nitrogen is selected as a limiting nutrient, the limiting concentration of the nitrogen can be, for example, 8.5 mM, 6.5 mM, 5 mM, 3.8 mM, 2.9 mM, 2.3 mM, 1.7 mM, 1.3 mM, 1 mM, 0.8 mM, or 0.6 mM. For embodiments in which phosphorous is selected as a limiting nutrient, the limiting concentration of the phosphorous can be, for example, 1.7 mM, 1.3 mM, 1 mM, 0.77 mM, 0.59 mM, 0.45 mM, 0.35 mM, 0.27 mM, 0.2 mM, 0.16 mM, or 0.12 mM.

In some embodiments, the controlling of the concentration of the selected limiting nutrients includes measuring the residual concentrations of the controlled nutrients. Based on the measured residual concentrations, a feeding of the nutrients to the population can be adjusted so as to maintain the residual concentration within a selected concentration range.

In some embodiments, the concentration of the selected limiting nutrients in at least one of the fermenters is measured offline by taking periodic samples and submitting said samples for standard analytical measurements such as chromatography and/or spectroscopy. In other embodiments, the concentration of the selected limiting nutrients in at least one of the fermenters is measured by utilizing a sampling port that is coupled to an online measuring apparatus that measures the concentration of the selected limiting nutrient.

In some embodiments, the controlling of the concentration of the selected limiting nutrients includes measuring the rate of population biomass production in at least one reactor of the fermentation system. Based on the measured biomass production rate, a feeding of the nutrients to the population can be adjusted so as to maintain the ratio of the nutrient feeding rate to the biomass production rate within a selected ratio range.

In some embodiments, the present disclosure is also directed to measuring and controlling the limited nutrient in at least one fermenter in which the aerobic biosynthesis occurs. The limiting nutrient feed rate can be controlled to maintain the desired limiting nutrient concentration in the fermenter to produce the desired yield of product. In some embodiments, the reactor system interacts with at least one control loop configured to measure and control limiting nutrient concentration in the fermentation liquid. The control loops can use feed forward controls, feedback controls, and combinations thereof.

The method can further include feeding at least one of the selected limiting nutrients to the population. In certain aspects, each of the selected limiting nutrients is fed to the population. The feeding can be performed continuously or intermittently. In certain aspects, at least one selected limiting nutrient is fed as a component of a gaseous feed stream. In certain aspects, at least one selected limiting nutrient is fed as a component of a liquid feed stream.

In some embodiments, the method further includes operating the fermentation system under continuous fermentation conditions suitable for synthesis of the extracellular product by the organism. In certain aspects, the continuous fermentation conditions are aerobic conditions. By operating the fermentation in a continuous fashion, many shortcomings of alternative batch and fed-batch fermentations can be mitigated or avoided entirely. For example, the discontinuous nature of batch and fed-batch processes inherently includes at least some fermentation downtime between cycles, during which the desired fermentations products are not being generated. An important consequence of this downtime is that the productivity of batch and fed-batch processes will be therefore reduced as compared to that of a continuous process. In addition, any operational variability between different cycles of a batch or fed-batch process can impact not only the amount, but also the quality, of the products being generated. This disadvantage is significantly reduced in continuous processes that are configured to operate with constant stead-state conditions.

In certain aspects, the continuous fermentation conditions include concentrations of the selected limiting nutrients that are less than their respective limiting concentrations in at least one reactor of the fermentation system. In certain aspects, the continuous fermentation conditions include concentrations of the selected limiting nutrients that are less than their respective limiting concentrations in each reactor of the fermentation system.

The continuous fermentation conditions can be such that the carbon in the fermentation is not limiting, e.g., the continuous fermentation conditions can include a carbon concentration greater than the limiting concentration for carbon in at least one reactor of the fermentation system.

In some embodiments, the continuous fermentation conditions include a population biomass concentration within a desired steady-state range. The continuous fermentation conditions can include a population biomass concentration that is, for example, between 10 g/L and 100 g/L, e.g., between 10 g/L and 64 g/L, between 19 g/L and 73 g/L, between 28 g/L and 82 g/L, between 37 g/L and 91 g/L, or between 46 g/L and 100 g/L. In terms of upper limits, the population biomass concentration of the continuous fermentation conditions can be less than 100 g/L, e.g., less than 91 g/L, less than 82 g/L, less than 73 g/L, less than 64 g/L, less than 55 g/L, less than 46 g/L, less than 37 g/L, less than 28 g/L, or less than 19 g/L. In terms of lower limits, the population biomass concentration of the continuous fermentation conditions can be greater than 10 g/L, e.g., greater than 19 g/L, greater than 28 g/L, greater than 37 g/L, greater than 46 g/L, greater than 55 g/L, greater than 64 g/L, greater than 73 g/L, greater than 82 g/L, or greater than 91 g/L. Higher concentrations, e.g., greater than 100 g/L, and lower concentrations, e.g., less than 10 g/L, are also contemplated.

In some embodiments, the yield of the extracellular product synthesized by the provided organism in the continuous fermentation conditions with limiting nutrient concentrations controlled to be lower than their respective limiting concentrations is increased relative to the yield under otherwise corresponding continuous fermentations with at least one selected limiting nutrient above its limiting nutrient concentration in each reactor of the fermentation system. The yield can be increased by, for example, more than 5%, e.g., more than 8%, more than 13%, more than 20%, more than 32%, more than 50%, more than 79%, more than 130%, more than 200%, more than 320%, or more than 500%. In certain aspects, the extracellular product is not synthesized by the organism under continuous fermentation conditions with at least one selected limiting nutrient above its limiting concentration in each reactor of the fermentation system.

In some embodiments, the productivity of the population biomass and/or the extracellular product in the continuous fermentation conditions with limiting nutrient concentrations controlled to be lower than their respective limiting concentrations is increased relative to the productivity under otherwise corresponding continuous fermentations with at least one selected limiting nutrient above its limiting nutrient concentration in each reactor of the fermentation system. The combined productivity of the population biomass and the extracellular product can be, for example, between 0.1 g/L/h and 10 g/L/h, e.g., between 0.1 g/L/h and 6 g/L/h, between 1 g/L/h and 7 g/L/h, between 2 g/L/h and 8 g/L/h, between 3 g/L/h and 9 g/L/h, or between 4 g/L/h and 10 g/L/h. In terms of upper limits, the combined productivity of the population biomass and the extracellular product can be less than 10 g/L/h, e.g., less than 9 g/L/h, less than 8 g/L/h, less than 7 g/L/h, less than 6 g/L/h, less than 5 g/L/h, less than 4 g/L/h, less than 3 g/L/h, less than 2 g/L/h, or less than 1 g/L/h. In terms of lower limits, the combined productivity of the population biomass and the extracellular product can be greater than 0.1 g/L/h, e.g., greater than 1 g/L/h, greater than 2 g/L/h, greater than 3 g/L/h, greater than 4 g/L/h, greater than 5 g/L/h, greater than 6 g/L/h, greater than 7 g/L/h, greater than 8 g/L/h, or greater than 9 g/L/h. Higher productivities, e.g., greater than 10 g/L/h, and lower productivities, e.g., less than 0.1 g/L/h, are also contemplated.

In some embodiments, the continuous fermentation conditions of the method further include the use of a cell retention device. As a non-limiting example, a cell retention strategy using a ceramic hollow fiber membrane can be employed to achieve and maintain a high cell density during fermentation.

In certain aspects, the culturing includes removing, either continuously or discretely, at least a portion of the population of the organism from one or more reactors of the fermentation system. The culturing can include removing at least some of the population from each reactor of the fermentation system. In some embodiments, the culturing of the population in the fermentation system includes recycling at least a portion of the population to at least one reactor of the fermentation system. In certain aspects, the recycled portion of the population is returned to the same one or more reactors from which the portion was removed. In certain aspects, the recycling of at least a portion of the population includes adding the population portion to one or more different reactors upstream from the one or more reactors from which the population portion was removed.

In some embodiments, the method further includes, prior to operating the fermentation system under the continuous fermentation conditions suitable for synthesis of the extracellular product, operating the fermentation system under growth conditions suitable for production of population biomass. The growth conditions are generally selected such that the yield of the population biomass is greater under the growth conditions than under the continuous fermentation conditions used for extracellular product synthesis. In certain aspects, the growth conditions include a concentration of at least one of the selected limiting nutrients above its limiting concentration in each reactor of the fermentation system. The concentration of the selected limiting nutrient need not be identical in each reactor of the fermentation system, as long as the concentration in each reactor is above the limiting concentration.

In some embodiments, the culturing of the population in the fermentation system includes supplying to the population one or more gases as feedstock components. Non-limiting examples of gases that can be supplied to population include carbon dioxide and hydrogen.

In some embodiments, the culturing of the population in the fermentation system includes supplying to the population one or more sugars as feedstock components. Non-limiting examples of sugars that can be supplied to population include glucose, xylose, and fructose.

In some embodiments, the culturing of the population in the fermentation system includes supplying to the population one or more sugar acids as feedstock components. A non-limiting example of a sugar acid that can be supplied to population is gluconate.

In some embodiments, the culturing of the population in the fermentation system includes supplying to the population one or more carboxylic acids as feedstock components. Non-limiting examples of carboxylic acids that can be supplied to population include propionic acid, lactic acid, formic acid, and lignocellulose-derived levulinic acid.

In some embodiments, the culturing of the population in the fermentation system includes supplying to the population one or more aromatics as feedstock components. Non-limiting examples of aromatics that can be supplied to population include phenol benzoic acid, and lignin-derived compounds such as benzoate analogues.

In some embodiments, the culturing of the population in the fermentation system includes supplying to the population one or more alcohols as feedstock components. Non-limiting examples of alcohols that can be supplied to population include glycerol, methanol, and ethanol.

In some embodiments, the carbon supplied to the population of the organism derives from a biological feedstock. The biological feedstock can be, or can derive from, monosaccharides, disaccharides, lignocellulose, hemicellulose, cellulose, paper-pulp waste, black liquor, lignin, levulinic acid and formic acid, triglycerides, glycerol, fatty acids, agricultural waste, thin stillage, condensed distillers' solubles, waste streams from the food processing or dairy industries, or municipal waste such as fruit peel/pulp or whey.

The feedstock source of the carbon supplied to the population can derive, for example, from a food industry waste stream or from an agricultural waste stream. Non-limiting examples of such waste streams include those of a brewing process, a dairy production process, a plant oil production process, an ethanol production process, a sugar production process, a corn processing plant, a soy processing plant, or a fish processing plant. The feedstock source of the carbon supplied to the population can also derive from a byproduct of a food industry process or of an agricultural process. In some embodiments, the carbon is derived from used cooking oil.

In some embodiments, the carbon supplied to the population of the organism derives from a non-biological feedstock. The non-biological feedstock can be, or can derive from, natural gas, syngas, a blend of carbon dioxide and hydrogen, carbon monoxide, hydrogen, oxygen, methanol, ethanol, waste streams from processes to produce monomers for the Nylon-66 and Nylon-6 industries such as but not limited to non-volatile residues (NVRs) or a caustic wash waste streams from the cyclohexane oxidation process used to manufacture adipic acid or caprolactam, or waste streams from other chemical industry processes such as, but not limited to processes associated with the carbon black industry, the hydrogen-refining industry, or the petrochemical industry. In some embodiments, the non-biological feedstock is a terephthalic acid (PTA) waste stream.

The methods can further include recovering the extracellular product from the fermentation system. Once the extracellular product has been produced, any suitable technique generally known in the art can be used to isolate the product from the system.

The present disclosure also provides bio-derived, bio-based, or fermentation-derived products produced using the methods and/or non-naturally occurring organisms disclosed herein. Examples of such products include, but are not limited to, compositions comprising at least one bio-derived, bio-based, or fermentation-derived compound or any combination thereof, as well as molded substances, formulations, and semi-solid or non-semi-solid streams comprising one or more of the bio-derived, bio-based, or fermentation-derived compounds or compositions, combinations, or products thereof.

The following embodiments are contemplated. All combinations of features and embodiments are contemplated.

Embodiment 1: A method for increasing the yield of an extracellular product in an aerobic fermentation system, the method comprising: providing an organism belonging to a genus selected from the group consisting of *Cupriavidus* and *Ralstonia*, wherein the organism has been modified to exhibit a decreased synthesis of polyhydroxyalkanoate relative to that of the corresponding wild type organism, wherein the organism has been modified to exhibit an increased synthesis of the extracellular product relative to that of the corresponding wild type organism, wherein the organism comprises one or more modified or exogenous promoters, and wherein the promoters are each independently a constitutive promoter or an inducible promoter activated by a nutrient limitation condition; culturing a population of the organism in the fermentation system; independently controlling the concentration of each of one or more selected limiting nutrients in at least one reactor of the fermentation system, wherein each limiting nutrient independently has a limiting concentration; and operating the fermentation system under continuous fermentation conditions suitable for synthesis of the extracellular product by the organism, wherein the continuous fermentation conditions comprise concentrations of the selected limiting nutrients less than their respective limiting concentrations in the at least one reactor, and wherein the yield of the extracellular product is increased relative to that synthesized by the organism under otherwise corresponding continuous fermentation conditions comprising concentrations of at least one of the selected limiting nutrients above its limiting concentration in each reactor of the fermentation system.

Embodiment 2: An embodiment of embodiment 1, wherein the selected limiting nutrients comprise nitrogen, phosphorous, iron, sulphate, potassium, oxygen, or a combination thereof.

Embodiment 3: An embodiment of embodiment 1 or 2, wherein the selected limiting nutrients comprise nitrogen having a limiting concentration of 5 mM.

Embodiment 4: An embodiment of any of the embodiments of embodiment 1-3, wherein the selected limiting nutrients comprise phosphorous having a limiting concentration of 1 mM.

Embodiment 5: An embodiment of any of the embodiments of embodiment 1-4, wherein the promoters are each independently a constitutive promoter or an inducible promoter activated by a nutrient limitation condition selected from the group consisting of a nitrogen limitation condition, a phosphorous limitation condition, and an oxygen limitation condition.

Embodiment 6: An embodiment of any of the embodiments of embodiment 1-5, wherein the organism is selected from the group consisting of *Cupriavidus necator, Cupriavidus metallidurans, Cupriavidus taiwanensis, Cupriavidus pinatubonensis, Cupriavidus basilensis,* and *Ralstonia pickettii*.

Embodiment 7: An embodiment of any of the embodiments of embodiment 1-6, wherein the continuous fermentation conditions further comprise a population biomass concentration between 10 g/L and 100 g/L.

Embodiment 8: An embodiment of any of the embodiments of embodiment 1-7, wherein the combined productivity of the population biomass and the extracellular product is greater than 0.5 g/L/h.

Embodiment 9: An embodiment of any of the embodiments of embodiment 1-8, wherein the fermentation system is selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced circulation, a bubble column fermenter, a fixed (packed)-bed column fermenter, a single horizontal fermenter having multiple compartments, and a multistage column fermenter.

Embodiment 10: An embodiment of any of the embodiments of embodiment 1-9 wherein the continuous fermentation conditions further comprise the use of a cell retention device.

Embodiment 11: An embodiment of any of the embodiments of embodiment 1-10, wherein the culturing comprises recycling at least a portion of the population to at least one reactor of the fermentation system.

Embodiment 12: An embodiment of any of the embodiments of embodiment 1-11, further comprising: prior to operating the fermentation system under the continuous fermentation conditions suitable for synthesis of the extracellular product, operating the fermentation system under growth conditions suitable for production of population biomass, wherein the yield of the population biomass is greater under the growth conditions than under the continuous fermentation conditions.

Embodiment 13: An embodiment of embodiment 12, wherein the growth conditions comprise a concentration of at least one of the selected limiting nutrients above its limiting concentration in each reactor of the fermentation system.

Embodiment 14: An embodiment of any of the embodiments of embodiment 1-13, wherein the culturing comprises feeding at least one of the selected limiting nutrients to the population, wherein the feeding is performed continuously.

Embodiment 15: An embodiment of any of the embodiments of embodiment 1-13, wherein the culturing comprises feeding at least one of the selected limiting nutrients to the population, wherein the feeding is performed intermittently.

Embodiment 16: An embodiment of embodiment 14 or 15, wherein the controlling comprises measuring the residual concentration of the at least one selected limiting nutrient in the at least one reactor and adjusting the feeding of the at least one selected limiting nutrient to maintain the residual concentration within a selected concentration range.

Embodiment 17: An embodiment of embodiment 16, wherein the measuring comprises sampling through a port coupled to an online measuring apparatus.

Embodiment 18: An embodiment of embodiment 14 or 15, wherein the controlling comprises measuring the rate of population biomass production in the at least one reactor and adjusting the feeding of the at least one selected limiting nutrient to maintain the ratio of the rate of feeding to the rate of population biomass production within a selected ratio range.

Embodiment 19: An embodiment of any of the embodiments of embodiment 16-18, wherein the measuring and the adjusting comprise operating a control loop, wherein the control loop uses feedback control, feed forward control, or a combination thereof.

Embodiment 20: An embodiment of any of the embodiments of embodiment 14-19, wherein the at least one selected limiting nutrient is fed as a component of a gaseous feed stream.

Embodiment 21: An embodiment of any of the embodiments of embodiment 14-19, wherein the at least one selected limiting nutrient is fed as a component of a liquid feed stream.

Embodiment 22: An embodiment of any of the embodiments of embodiment 1-21, wherein the culturing further comprises supplying to the population one or more feedstock components selected from the list consisting of gases, sugars, sugar acids, carboxylic acids, aromatics, and alcohols.

Embodiment 23: An embodiment of embodiment 22, wherein the gases are selected from the group consisting of carbon dioxide and hydrogen; wherein the sugars are selected from the group consisting of glucose, xylose, and fructose; wherein the sugar alcohols consist of gluconate; wherein the carboxylic acids are selected from the group consisting of propionic acid, lactic acid, and formic acid; wherein the aromatics are selected from the group consisting of phenol and benzoic acid; and wherein the alcohols consist of glycerol.

Embodiment 24: An embodiment of any of the embodiments of embodiment 1-23, wherein the continuous fermentation conditions further comprise a concentration of carbon greater than its limiting concentration in the at least one reactor.

Embodiment 25: An embodiment of embodiment 24, wherein the carbon derives from a biological feedstock.

Embodiment 26: An embodiment of embodiment 24, wherein the carbon derives from a non-biological feedstock.

Embodiment 27: An embodiment of embodiment 25 or 26, wherein the feedstock derives from a food industry waste stream or an agricultural industry waste stream.

Embodiment 28: An embodiment of any of the embodiments of embodiment 1-27, wherein the extracellular product comprises a $C_{3-12}$ organic acid, an alcohol, an olefin, a hydroxyacid, a fatty acid, an amino acid, an alkane, an alkene, an isoprenoid, an amine, or a combination thereof.

Embodiment 29: An embodiment of any of the embodiments of embodiment 1-27, wherein the extracellular product comprises a $C_{6-12}$ difunctional aliphatic fatty acid or a derivative thereof, a $C_{6-12}$ amino acid, a $C_{6-12}$ diamine, a $C_{6-12}$ hydroxyacid, a $C_{6-12}$ diol, a $C_{6-12}$ diacid, or a combination thereof.

Embodiment 30: An embodiment of any of the embodiments of embodiment 1-27, wherein the extracellular product comprises methionine, threonine, lysine, glutamic acid, tryptophan, aspartic acid, citric acid, maleic acid, succinic acid, isoprene, linalool, limonene, 3-hydroxypropanoic acid, 1,2-propanediol, 1,3-propanediol, malonic acid, lactic acid, n-butanol, 2-butanone, butadiene, 2,3-butanediol, 1,3-butanediol, benzoic acid, 1,4-benzenediamine, benzeneamine, pentamethylene diamine, 1,4-diaminobutane, 2-hydroxyisobutyric acid, itaconic acid, or a combination thereof.

Embodiment 31: A non-naturally occurring organism belonging to a genus selected from the group consisting of *Cupriavidus* and *Ralstonia*, wherein the organism has been modified to exhibit a decreased synthesis of polyhydroxybutyrate relative to that of the corresponding wild type organism, wherein the organism has been modified to exhibit an increased synthesis of an extracellular product relative to that of the corresponding wild type organism, wherein the organism comprises one or more modified or exogenous promoters, wherein the promoters are each independently an inducible promoter activated by a nutrient limitation condition, and wherein synthesis of the extracellular product by the organism is increased when the inducible promoters are activated.

Embodiment 32: An embodiment of embodiment 31, wherein the promoters are each independently an inducible promoter activated by a nutrient limitation condition selected from the group consisting of a nitrogen limitation condition, a phosphorous limitation condition, and an oxygen limitation condition.

Embodiment 33: An embodiment of embodiment 31 or 32, wherein the organism is selected from the group consisting of *Cupriavidus necator, Cupriavidus metallidurans, Cupriavidus taiwanensis, Cupriavidus pinatubonensis, Cupriavidus basilensis*, and *Ralstonia pickettii*.

Embodiment 34: An embodiment of any of the embodiments of embodiment 31-33, wherein the extracellular product comprises a $C_{3-12}$ organic acid, an alcohol, an olefin, a hydroxyacid, a fatty acid, an amino acid, an alkane, an alkene, an isoprenoid, an amine, or a combination thereof.

Embodiment 35: An embodiment of any of the embodiments of embodiment 31-33, wherein the extracellular product comprises a $C_{6-12}$ difunctional aliphatic fatty acid or a derivative thereof, a $C_{6-12}$ amino acid, a $C_{6-12}$ diamine, a $C_{6-12}$ hydroxyacid, a $C_{6-12}$ diol, a $C_{6-12}$ diacid, or a combination thereof.

Embodiment 36: An embodiment of any of the embodiments of embodiment 31-33, wherein the extracellular product comprises methionine, threonine, lysine, glutamic acid, tryptophan, aspartic acid, citric acid, maleic acid, succinic acid, isoprene, linalool, limonene, 3-hydroxypropanoic acid, 1,2-propanediol, 1,3-propanediol, malonic acid, lactic acid, n-butanol, 2-butanone, butadiene, 2,3-butanediol, 1,3-butanediol, benzoic acid, 1,4-benzenediamine, benzeneamine, pentamethylene diamine, 1,4-diaminobutane, 2-hydroxyisobutyric acid, itaconic acid, or a combination thereof.

Embodiment 37: An extracellular product made using the method of an embodiment of any of the embodiments of embodiment 1-27.

Embodiment 38: An embodiment of embodiment 37, wherein the extracellular product comprises a $C_{3-12}$ organic acid, an alcohol, an olefin, a hydroxyacid, a fatty acid, an amino acid, an alkane, an alkene, an isoprenoid, an amine, or a combination thereof.

Embodiment 39: An embodiment of embodiment 37, wherein the extracellular product comprises a $C_{6-12}$ difunctional aliphatic fatty acid or a derivative thereof, a $C_{6-12}$ amino acid, a $C_{6-12}$ diamine, a $C_{6-12}$ hydroxyacid, a $C_{6-12}$ diol, a $C_{6-12}$ diacid, or a combination thereof.

Embodiment 40: An embodiment of embodiment 37, wherein the extracellular product comprises methionine, threonine, lysine, glutamic acid, tryptophan, aspartic acid, citric acid, maleic acid, succinic acid, isoprene, linalool, limonene, 3-hydroxypropanoic acid, 1,2-propanediol, 1,3-propanediol, malonic acid, lactic acid, n-butanol, 2-butanone, butadiene, 2,3-butanediol, 1,3-butanediol, benzoic acid, 1,4-benzenediamine, benzeneamine, pentamethylene diamine, 1,4-diaminobutane, 2-hydroxyisobutyric acid, itaconic acid, or a combination thereof.

EXAMPLES

The present disclosure will be better understood in view of the following non-limiting example.

Example 1

Nitrogen Limitation

Under nitrogen limitation in the presence of excess carbon, *C. necator* produces large amounts of PHB (up to 80% of the cell weight). In a strain deficient in PHB synthesis, under nitrogen limitation in the presence of excess carbon, there is excretion of large amounts of pyruvate into the media. Also, there is a greater concentration of the reducing-cofactor NADH. In *C. necator* these conditions have been used to produce branched-chain alcohols (Lu et al. Appl. Microbiol. Biotechnol. 2012 96(1):283-297), 2-HIBA (Przybylski et al. Appl. Microbiol. Biotechnol. 2013 97(20): 8875-85), isopropanol (Grousseau et al. Appl. Microbiol. Biotechnol. 2014 98(9):4277-90), and ethanol (Lee et al. Biotechnology and Bioprocess Engineering 2016 21:402-407), among others.

In *C. necator*, a ΔphaC1 strain expressing *Bacillus massiliosenegalensis* MeaB, RcmA and RcmB for the production of 2-HIBA showed an increase in the production of this compound under nitrogen limiting conditions (~2-fold). Also in *C. necator*, a ΔphaCAB Δicd1 Δicd2 expressing *Aspergillus terreus* cad1 for the production of itaconic acid, derived from the TCA cycle, showed an increase in the production of this compound under nitrogen limiting conditions (~7-fold).

Example 2

ΔphaCAB *C. necator* H16 Nitrogen Limitation Promoting Isopropanol Producing Strain A ΔphaCAB *C. necator* H16 strain was used to demonstrate production of isopropanol under a nitrogen-limitation constitutive promoter. Said *C. necator* H16 strain was further modified to eliminate A0006-9 encoding endonucleases, thereby improving transformation efficiency as described in U.S. patent application Ser. No. 15/717,216, teachings of which are incorporated herein by reference. The IPA pathway was integrated into this *C. necator* strain (Grousseau et al. 2014).

In particular, the following genes were integrated: *C. necator* β-ketothiolase A bktB (H16_A1445), the two-sub-unit succinyl-coA transferase (H16_A1331, H16_A1332), *C. acetobutylicum* acetoacetate decarboxylase (CA_P0165), and *C. beijerinckii* alcohol dehydrogenase (AF157307). This final pathway gene, *C. beijerinckii* alcohol dehydrogenase (AF157307) was amplified with a strong ribosome binding site (RBS)

(TAAAGGAGGTGAAGC (SEQ ID NO: 1))

upstream of the start codon. The pathway contains a constitutive pTac promoter:

(SEQ ID NO: 2)
GAGCTGTTGACAATTAATCATCGGCTCGTATAATGTGTGGAATTGTGAGC

GGATAACAATTTCACACA.

Each of these genes were cloned into a plasmid which was integrated into *C. necator* BDISC2181 using the phiC31 integrase method.

Example 3

Nitrogen Limitation Promoting Isopropanol (IPA) Production in *C. necator* H16 Strain The recombinant strain from Example 2, with the ability to constitutively produce isopropanol and the precursor molecule, acetone, was grown on a fructose based medium with ammonium sulphate as a source of nitrogen. Continuous culture was used to compare four different steady state conditions, each with a different concentration of fed ammonium sulphate (incrementally lowered in order to examine nitrogen limitation). The conditions were tested with the recombinant ΔphaCAB H16 strain containing the integrated isopropanol plasmid. Growth was established at a dilution rate of D=0.05 h$^{-1}$, a temperature of 30° C., and a pH of 6.6 in a volume maintained at 0.8 L. Four replicate vessels were run for the strain, and two samples were taken under each steady state, resulting in eight data points used to establish a mean and standard deviation. For each steady state, concentrations were measured of biomass (dry cell weight and OD600), residual nitrogen and carbon, and product isopropanol and acetone (determination via liquid chromatography). Oxygen uptake rate and carbon dioxide emission rate, were also determined.

Residual nitrogen concentration was determined to decrease to >8 mM when feeding 14 g/L ammonium sulphate. At 14 g/L ammonium sulfate, 96.5% of the mass and 95% of the carbon in the total product (isopropanol, acetone and biomass) goes into biomass production. As shown in Table 1, decreasing the residual concentration to below 5 mM decreases the overall productivity rate (row 8) but increases specific productivity (mg product/L/h/g dry cell weight, rows 9-12) and the percentage of mass and carbon going into isopropanol and acetone (rows 13 and 14). Utilization of cell recycle during the fermentation would allow for increased overall steady state biomass concentration that would result in the overall production rate of IPA and acetone to increase proportionally to the biomass concentration. Residual fructose concentrations also increased as nitrogen limitation increased, although there was no significant difference observed between the strains. The carbon evolution rate (CER) and oxygen uptake rate (OUR) were both found to decrease as the amount of ammonium sulphate in the feed was also decreased (data not shown).

TABLE 1

Isopropanol production in *C. necator* under nitrogen limitation at D = 0.1 h$^{-1}$

| Ammonium sulphate feed concentration (g/L) | 14 | 7 | 3.5 | 1.75 |
|---|---|---|---|---|
| Nitrogen feed rate (mM/h) | 10.8 | 5.4 | 2.7 | 1.3 |
| Residual NH$_3$ concentration (mM) | >8 | 2.8 | 1.8 | — |
| Biomass concentration (g/L) | 20.4 | 15.0 | 8.7 | 7.9 |
| Isopropanol productivity (g/L/h) | 0.04 | 0.12 | 0.07 | 0.03 |
| Acetone productivity (g/L/h) | 0.00 | 0.01 | 0.01 | 0.01 |
| Biomass productivity (g/L/h) | 1.02 | 0.75 | 0.43 | 0.40 |
| Combined product productivity (g/L/h) | 1.06 | 0.87 | 0.51 | 0.44 |
| Isopropanol specific productivity (g/L/h/g DCW) | 1.71 | 7.71 | 7.86 | 3.94 |
| Acetone specific productivity (g/L/h/g DCW) | 0.14 | 0.43 | 1.16 | 0.94 |
| Biomass specific productivity (g/L/h/g DCW) | 49.93 | 49.87 | 49.71 | 50.83 |
| Combined product specific productivity (g/L/g DCW) | 51.78 | 58.01 | 58.73 | 55.71 |
| Percent combined productivity in isopropanol/acetone | 3.6% | 14.0% | 15.4% | 8.8% |
| Percent combined carbon in isopropanol/acetone | 4.6% | 17.6% | 19.2% | 11.2% |

Example 4

Phosphate Limitation

The effects of phosphate limitation in the presence of excess carbon are generally similar to those observed for nitrogen limitation. In a strain deficient in PHB synthesis this limitation condition has also been used for the production of branched-chain alcohols (Lu et al. Appl. Microbiol. Biotechnol. 2012 96(1):283-97), amongst others. In *E. coli*, under phosphate limiting conditions, genes involved in glycolysis and the pentose phosphate pathway are upregulated. In contrast, the majority of the genes of the TCA cycle are downregulated. Also, several amino acid degradation pathways are upregulated, resulting in the generation of NADH, NADPH, and $CO_2$ (Youngquist et al. J. Ind. Microbiol. Biotechnol. 2017 44:759-772).

In *C. necator*, a ΔphaC1 strain expressing *Bacillus massiliosenegalensis* MeaB, RcmA and RcmB for the production of 2-HIBA showed an increase in the production of this compound under phosphorus limiting conditions (~1.2-fold). In *C. necator*, a ΔphaCAB Δicd1 Δicd2 expressing *Aspergillus terreus* cad1 for the production of itaconic acid, derived from the TCA cycle, showed an increase in the production of this compound under phosphorus limiting conditions (~3.5-fold). In *C. necator*, under phosphorus limitation during continuous gas fermentation, a ΔphaCAB strain expressing *C. necator* phaA (H16_A1438), *C. necator* H16_A1331/2, *Clostridium acetobutylicum* adc and *Clostridium beijerinkii* adh produced large quantities of isopropanol and acetone, while this strain showed lower biomass productivity as compared to the wild type and the ΔphaCAB strains, suggesting that more acetyl-CoA and NADPH are diverted from growth to product synthesis.

Example 5

Oxygen Limitation

Under oxygen limitation, the NADH/NAD ratio increases. A higher amount of NADH inhibits the citrate synthase and the isocitrate dehydrogenase, blocking the TCA cycle. The accumulation of acetyl-CoA triggers the production of PHB. In *C. necator* there is accumulation of PHB under oxygen limitation conditions (Du et al. World Journal of Microbiology & Biotechnology 2000 16:9-13). Therefore, in a strain deficient in PHB synthesis, the effects would be the same as the ones observed under nitrogen and phosphate limitation. The excess carbon could be redirected to the production of other compounds.

Example 6

Carbon Limitation

Under carbon limitation conditions, use of substrate carbon for production of extracellular products is reduced. Under carbon limitation conditions, cells can increase the concentration of a transport system for a variety of carbon substrates (Harder, W., & Dijkhuizen, L. Annu. Rev. Microbiol. 1983 37:1-23). This condition could be used to increase the uptake and utilization of different carbon feedstocks. Carbon limitation in combination with oxygen and/or nitrogen and/or phosphorus and/or iron and/or sulphur and/or potassium limitation could be use in a strain deficient in PHB synthesis for the production of a target product once enough biomass has been accumulated.

Example 7

Iron Limitation

Iron limitation affects the synthesis and function of iron-sulfur proteins and cytochromes, components of the electron transport chain. The electron transport chain (ETC) can then be affected. Glycolysis can be upregulated to generate more ATP, but as the ETC is affected, NADH can accumulate increasing the ratio NADH/NAD+. Then, the TCA cycle (that generates 3 NADH and 1 $FADH_2$, or 1 NADPH, 2 NADH and 1 $FADH_2$ in *C. necator*) slows down. Growth rate is also lower under iron limiting conditions.

In *E. coli*, those pathways not requiring iron, or requiring only small amounts, are upregulated, while those that need iron are downregulated. For example, glycolysis is upregulated, and TCA cycle and respiratory metabolism are down-regulated (Folsom et al. J. Bacteriol. 2014 196(15):2748-61). In *E. coli*, under iron limitation there is an increase in organic by-products excreted into the media such as acetate, lactate, pyruvate, and formate. The relative abundance of each of these by-products varies depending on the amount of iron present in the media (Folsom et al. J. Bacteriol. 2014 196(15):2748-61).

In *C. necator*, glycolysis is performed using the Entner-Doudoroff pathway. This pathway does not require iron. Similar effects as those observed in *E. coli* would be expected. The by-products could be redirected for the synthesis of other compounds by expression of heterologous pathways.

Example 8

Potassium Limitation

Potassium is an important nutrient as it is required for pH homeostasis. In *E. coli*, potassium limitation affects growth, glucose consumption, and oxygen consumption (Weiden et al. J. Gen. Physiol. 1967 50(6):1641-61; Schramke et al. Microbiologyopen 2017 6(3)). In *E. coli*, when potassium is limiting in the media the content of potassium and phosphorus in the cell drops (Weiden et al. J. Gen. Physiol. 1967 50(6):1641-61; Schramke et al. Microbiologyopen 2017 6(3) doi: 10.1002/mbo3.438). A limitation of potassium in the media is expected to have similar effects in *C. necator*.

Example 9

Sulphur Limitation

In *E. coli*, sulphur limitation upregulates the cysteine and the methionine biosynthetic pathways (Gyaneshwar et al., 2005). In *E. coli*, sulphur limitation increases oxidative stress (Gyaneshwar et al. J. Bacteriol. 2005 187(3):1074-90). In *E. coli*, sulphur limitation upregulates the expression of the glycine cleavage system resulting in carbon dioxide, ammonia, and $C_1$ groups. Also, sulphur limitation increases the transcription of serA, catalyzing the first step for serine biosynthesis. Serine can then be converted into glycine by GlyA (Gyaneshwar et al. J. Bacteriol. 2005 187(3):1074-90).

Sulphur limitation affects the synthesis and function of iron-sulphur proteins and cytochromes, components of the electron transport chain. The electron transport chain (ETC) could then be affected. Glycolysis could then be upregulated to generate more ATP, but as the ETC is affected, NADH can accumulate increasing the ratio of NADH/NAD+. Then, the TCA cycle that generates 3 NADH and 1 $FADH_2$ (or 1 NADPH, 2 NADH and 1 $FADH_2$ in *C. necator*) would slow down.

Example 10

Phosphorous and Carbon Limitation

Under phosphorus limitation conditions, it seems that low levels of carbon have a positive effect on PHB accumulation in *C. necator* (Shang et al. Biotechnol. Lett. 2003 25(17): 1415-9). This could be due to a slow-down of the TCA cycle and a decrease in the free CoA concentration. This can be used in a strain of *R. eutropha* deficient in PHB synthesis for the production of other products.

Example 11

Nitrogen Limitation Inducible Promoters

A set of putative *C. necator* nitrogen-limitation inducible promoters were identified by RNAseq data from strains grown under nitrogen-limiting conditions. These include a promoter of the H16_A0359 gene which encodes a nitrate ABC transporter substrate-binding protein (GenBank ID WP_010814804.1). In a pBBR1-based test context, the H16_A0359 promoter activity was greatest at a concentration of 0 g/l ammonium chloride, and its activity decreased as the ammonium chloride concentration was increased, up to 0.6 g/L. Promoters of the H16_B1109 gene, A0319 gene and A1075 gene, among others, are used.

Example 12

Phosphate Limitation Inducible Promoters

The PhnG promoter corresponds to the intergenic region between the two divergently oriented genes phnF and phnG of *C. necator* H16 (chromosome-2). This enzyme is involved in phosphonate metabolism (the identical protein GenBank ID KUE89182.1 has been identified as "phosphonate C-P lyase system protein PhnG"). The structure of the operon and annotation on similar proteins indicate that the regulation of this promoter may involve the upstream regulator protein PhnF. The phnG promoter was induced at phosphate concentrations of 0.02 g/L and below in both pMOL28 and pBBR1 contexts. Additional promoters include $P_{phoA}$ ($P_{H16\_A2183}$) and $P_{pstS}$, both involved in phosphate metabolism, and $P_{phnC1}$ ($P_{H16\_B1296}$) and $P_{phnF}$, both involved in phosphate transport.

Example 13

Oxygen Limitation Inducible Promoters

Examples of oxygen-limitation inducible promoters include $P_{ccoN}$ (PH16_A2319), $P_{cydA1}$ (PH16_B1177), and $P_{cydA2}$ (PH16_B1461).

Example 14

Use of Nutrient Limitation Inducible Promoters Under Nutrient Limitation Conditions A *C. necator* of the H16 strain with at least a portion of the phaCAB gene locus, involved in PHB production, was used to demonstrate production of isopropanol under a phosphorus-limitation inducible promoter. The *C. necator* H16 strain was further modified to eliminate A0006-9 encoding endonucleases, thereby improving transformation efficiency as described in U.S. patent application Ser. No. 15/717,216, teachings of which are incorporated herein by reference. The IPA pathway was integrated into this *C. necator* strain (Grousseau et al.).

In particular, the following genes were integrated via a plasmid: *C. necator* β-ketothiolase A bktB (H16_A1445), the two-subunit succinyl-coA transferase (H16_A1331, H16_A1332), *C. acetobutylicum* acetoacetate decarboxylase (CA_P0165), and *C. beijerinckii* alcohol dehydrogenase (AF157307). This final pathway gene, *C. beijerinckii* alcohol dehydrogenase (AF157307) was amplified with a strong ribosome binding site (RBS) (TAAAGGAGGTGAAGC (SEQ ID NO: 1)) upstream of the start codon. The pathway was under the control of a constitutive pTac promoter: GAGCTGTTGACAATTAAT-CATCGGCTCGTATAATGTGTGGAATTGTGAGCGGA-TAAC AATTTCACACA (SEQ ID NO: 2). The pathway was integrated into *C. necator* BDISC2181 using the phiC31 integrase method.

The native $P_{phnG}$ promoter (i.e., intergenic sequence between H16_B1229 and H16_B1228; CTCGCGCTGCCCTCTTGTCATCAAGCGTTCACCAT-TGCCATGCGATTGTGCCTCAACC GCGCCGC-GATGGCGGGGTGCCCGAGCAATGCCCCGCCCCGT-CATGAAACGTTCATC TGCCTGTGGTCTAGTAGCTGCGTGTT-CAAGCAGTGACATCTAAACGTATA (SEQ ID NO: 3)) was fused to the bktB (H16_A1445) ribosome binding site (ATGGAGACAAAGTC (SEQ ID NO: 4)) and coding sequence, the two-subunit succinyl-coA transferase (H16_A1331, H16_A1332), *C. acetobutylicum* acetoacetate decarboxylase (CA_P0165) and *C. beijerinckii* alcohol dehydrogenase (AF157307), as per Grousseau et al. The phaC1AB1 operon in chromosome 1 was substituted with the $P_{phnG}$-IPA pathway by 2-step homologous recombination, using tetracycline resistance to select for the first recombination event and sacB-mediated counter-selection to select for the second recombination event.

Figure 2:
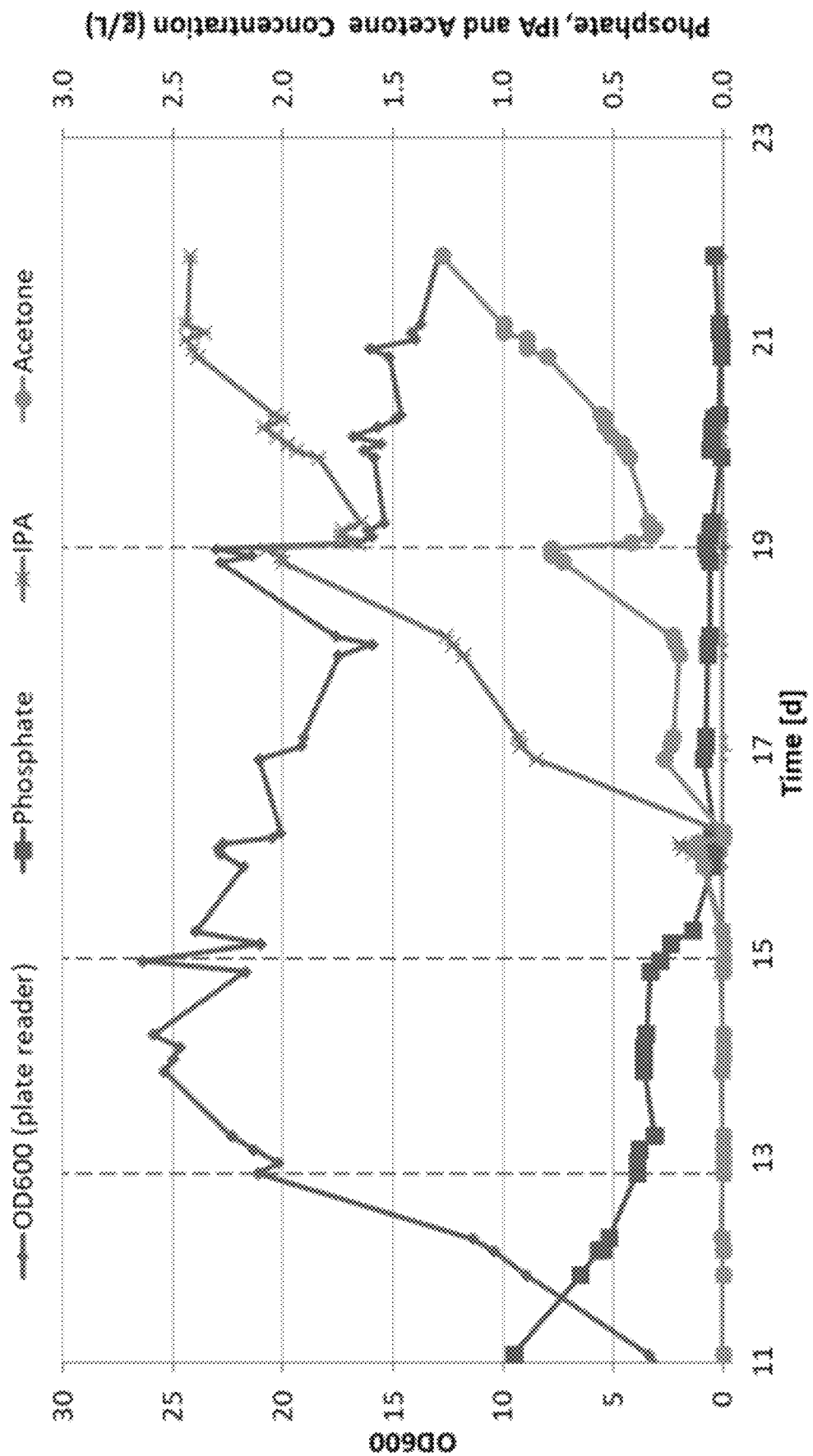
FIG. 2 is a graph showing reactor conditions for isopropanol production by an organism having a phosphorous-limitation inducible promoter and cultured under limited phosphate in a CSTR.

A culture of the aforesaid *C. necator* strain was grown in an 80-L loop bioreactor maintained at a gauge pressure of 3.5 bar. The culture medium was a minimal medium broth that was pH controlled at pH 6.6, and foam controlled to maintain a 30% gas hold up. A feed gas of air supplemented with hydrogen at a concentration of 52% (v/v) and carbon dioxide at a concentration of 4% (v/v) was added to the bioreactor at a feed rate of 1.27 standard liter/minute. This level of hydrogen in excess of that needed to support culture growth and maintenance and product biosynthesis. The oxygen concentration in the bioreactor headspace was maintained at less than 4% (v/v), and the oxygen uptake rate of the culture was maintained from 150 mM/h to 175 mM/h. Phosphoric acid was added as a phosphorous nutrient source to maintain a residual phosphate level at less than 0.1 g/L (1mM phosphorous) as measured by liquid chromatography. Phosphate was thereby slightly limited relative to oxygen to improve IPA selectivity. The dissolved oxygen level of the culture was set to maintain oxygen limitation. Concentration measurements from the reactor are presented in the graph of FIG. 1. A similar strategy was also applied to a continuous stirred tank reactor (CSTR), with certain parameters adjusted according to the different mass transfer capacity of the CSTR. Results from this continuous fermentation are presented in the graph of FIG. 2.

While the disclosure has been described in detail, modifications within the spirit and scope of the disclosure will be readily apparent to those of skill in the art. It should be understood that aspects of the disclosure and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only and is not intended to limit the disclosure. All patents and publications cited herein are incorporated by reference in their entirety for all purposes.

We claim:

1. A method for increasing the yield of an extracellular product in an aerobic fermentation system, the method comprising:
   providing an organism belonging to a genus selected from the group consisting of *Cupriavidus* and *Ralstonia*, wherein the organism has been modified to exhibit a decreased synthesis of polyhydroxyalkanoate relative to that of the corresponding wild type organism, wherein the organism has been modified to exhibit an increased synthesis of the extracellular product relative to that of the corresponding wild type organism, wherein the organism comprises promoters comprising the genetic sequences of SEQ ID No. 2 and SEQ ID No, 3 and wherein the organism is modified to increase the efflux or secretion of the extracellular product by altering a structure of the organism's cell membrane, increasing or introducing active or passive transporter activity related to the export of the extracellular product, or a combination thereof;
   culturing a population of the organism in the fermentation system;
   independently controlling the concentration of each of one or more selected limiting nutrients in at least one reactor of the fermentation system, wherein each limiting nutrient independently has a limiting concentration; and
   operating the fermentation system under continuous fermentation conditions suitable for synthesis of the extracellular product by the organism, wherein the continuous fermentation conditions comprise concentrations of the selected limiting nutrients less than their respective limiting concentrations in the at least one reactor, and wherein the yield of the extracellular product is increased relative to that synthesized by the organism under otherwise corresponding continuous fermentation conditions comprising concentrations of at least one of the selected limiting nutrients above its limiting concentration in each reactor of the fermentation system, wherein the continuous fermentation conditions comprise a population biomass concentration between 10 g/L and 100 g/L, wherein
   the organism is initially provided a feedstock comprising carbon, supplied to the organism is derived from natural gas, syngas, a blend of carbon dioxide and hydrogen, carbon monoxide methanol, ethanol, industrial waste streams, or a mixture thereof.

2. The method of claim 1, wherein the selected limiting nutrients comprise nitrogen, phosphorous, iron, sulphate, potassium or a combination thereof.

3. The method of claim 1, wherein the selected limiting nutrients comprise nitrogen having a limiting concentration of 5 mM.

4. The method of claim 1, wherein the selected limiting nutrients comprise phosphorous having a limiting concentration of 1 mN.

5. The method of claim 1, wherein the promoters are each independently a constitutive promoter or an inducible promoter activated by a nutrient limitation condition selected from the group consisting of a nitrogen limitation condition, a phosphorous limitation condition, and an oxygen limitation condition.

6. The method of claim 1, wherein the organism is selected from the group consisting of *Cupriavidus necator,*

*Cupriavidus metallidurans, Cupriavidus taiwanensis, Cupriavidus pinatubonensis, Cupriavidus basilensis,* and *Ralstonia pickettii.*

7. The method of claim 1, wherein the combined productivity of the population biomass and the extracellular product is in a range of from 0.1 g/L/h to 6 g/L/h.

8. The method of claim 1, wherein the fermentation system is selected from the group consisting of a single fermenter, multiple fermenters in series, a membrane fermenter, a fixed-bed fermenter, a fluidized-bed fermenter, a plug flow fermenter, a pneumatically agitated fermenter, a gas-lift fermenter with an external loop having forced circulation, a bubble column fermenter, a fixed-bed column fermenter, a single horizontal fermenter having multiple compartments, and a multistage column fermenter.

9. The method of claim 1 wherein the continuous fermentation conditions further comprise the use of a cell retention device.

10. The method of claim 1, wherein the culturing comprises recycling at least a portion of the population to at least one reactor of the fermentation system.

11. The method of claim 1, further comprising:
    prior to operating the fermentation system under the continuous fermentation conditions suitable for synthesis of the extracellular product, operating the fermentation system under growth conditions suitable for production of population biomass, wherein the yield of the population biomass is greater under the growth conditions than under the continuous fermentation conditions.

12. The method of claim 11, wherein the growth conditions comprise a concentration of at least one of the selected limiting nutrients above its limiting concentration in each reactor of the fermentation system.

13. The method of claim 1, wherein the culturing comprises feeding at least one of the selected limiting nutrients to the population; and wherein the controlling comprises:
    measuring the residual concentration of the at least one selected limiting nutrient in the at least one reactor, and
    adjusting the feeding of the at least one selected limiting nutrient to maintain the residual concentration within a selected concentration range.

14. The method of claim 13, wherein the measuring comprises sampling through a port coupled to an online measuring apparatus.

15. The method of claim 1, wherein the culturing comprises feeding at least one of the selected limiting nutrients to the population; and wherein the controlling comprises:
    measuring the rate of population biomass production in the at least one reactor, and
    adjusting the feeding of the at least one selected limiting nutrient to maintain the ratio of the rate of feeding to the rate of population biomass production within a selected ratio range.

16. The method of claim 1, wherein the organism further comprises the following genes integrated into the organism's genome β-ketothiolase A bktB (H16_A1445), the two-subunit succinyl-coA transferase (H16_A1331, H16_A1332), *C. acetobutylicum* acetoacetate decarboxylase (CA_P0165), and *C. beijerinckii* alcohol dehydrogenase (AF157307).

\* \* \* \* \*

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taaaggaggt gaagc                                                     15
```

```
<210> SEQ ID NO 2
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagctgttga caattaatca tcggctcgta taatgtgtgg aattgtgagc ggataacaat     60
ttcacaca                                                             68

<210> SEQ ID NO 3
<211> LENGTH: 164
<212> TYPE: DNA
<213> ORGANISM: Cupriavidus necator

<400> SEQUENCE: 3
ctcgcgctgc cctcttgtca tcaagcgttc accattgcca tgcgattgtg cctcaaccgc    60
gccgcgatgg cggggtgccc gagcaatgcc ccgccccgtc atgaaacgtt catctgcctg   120
tggtctagta gctgcgtgtt caagcagtga catctaaacg tata                    164

<210> SEQ ID NO 4
<211> LENGTH: 14
<212> TYPE: DNA
<213> ORGANISM: Cupriavidus necator

<400> SEQUENCE: 4
atggagacaa agtc                                                      14
```